United States Patent
Scates et al.

(10) Patent No.: US 9,505,696 B2
(45) Date of Patent: *Nov. 29, 2016

(54) PROCESS TO CONTROL HI CONCENTRATION IN RESIDUUM STREAM

(71) Applicant: Celanese International Corporation, Dallas, TX (US)

(72) Inventors: Mark O Scates, Houston, TX (US); Ronald David Shaver, Houston, TX (US); Yaw-Haw Liu, Missouri City, TX (US)

(73) Assignee: Celanese International Corporation, Dallas, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/874,012

(22) Filed: Oct. 2, 2015

(65) Prior Publication Data

US 2016/0221919 A1    Aug. 4, 2016

Related U.S. Application Data

(63) Continuation-in-part of application No. 14/724,197, filed on May 28, 2015.

(60) Provisional application No. 62/112,120, filed on Feb. 4, 2015.

(51) Int. Cl.
*C07C 51/44* (2006.01)
*B01D 3/16* (2006.01)
(Continued)

(52) U.S. Cl.
CPC .............. *C07C 51/44* (2013.01); *B01D 3/009* (2013.01); *B01D 3/16* (2013.01); *B01D 3/34* (2013.01); *B01D 3/4283* (2013.01); *C07C 51/12* (2013.01)

(58) Field of Classification Search
CPC ........ B01D 3/16; B01D 3/34; B01D 3/4283; C07C 51/44
See application file for complete search history.

(56) References Cited

U.S. PATENT DOCUMENTS 3,769,329 A    10/1973   Paulik et al.
3,772,156 A    11/1973   Johnson et al.
(Continued)

FOREIGN PATENT DOCUMENTS

CN    1349855 A    5/2002
CN    1640843 A    7/2005
(Continued)

OTHER PUBLICATIONS

"The Cativa .TM.Process for the Production of Acetic Acid", Chem. Ind. (Dekker) 1998, 75 Catalysis of Organic Reactions of Derrick J. Watson, pp. 369-380.

(Continued)

*Primary Examiner* — In Suk Bullock
*Assistant Examiner* — Jonathan Miller
(74) *Attorney, Agent, or Firm* — Mark L. Copper; Cooper & Assoc.

(57) ABSTRACT

A process directed to acetic acid production comprising providing a feed stream having a first density comprising water, acetic acid, methyl acetate, at least one PRC, and greater than about 30 wt % methyl iodide to a distillation column comprising a distillation zone and a bottom sump zone; and distilling the feed stream at a pressure and a temperature sufficient to produce an overhead stream having a second density and comprising greater than about 40 wt % methyl iodide and at least one PRC; wherein a percent decrease between the first density and the second density is from 20% to 35%.

18 Claims, 4 Drawing Sheets

(51) Int. Cl.
*C07C 51/12* (2006.01)
*B01D 3/00* (2006.01)
*B01D 3/42* (2006.01)
*B01D 3/34* (2006.01)

(56) References Cited

U.S. PATENT DOCUMENTS

| | | | |
|---|---|---|---|
| 3,791,935 A | 2/1974 | Eubanks et al. | |
| 4,039,395 A | 8/1977 | Eby | |
| 4,139,688 A | 2/1979 | Dixon | |
| 4,255,591 A | 3/1981 | Makin et al. | |
| 4,615,806 A | 10/1986 | Hilton | |
| 4,786,699 A | 11/1988 | Nuber et al. | |
| 4,994,608 A | 2/1991 | Torrence et al. | |
| 5,001,259 A | 3/1991 | Smith et al. | |
| 5,026,908 A | 6/1991 | Smith et al. | |
| 5,139,981 A | 8/1992 | Kurland | |
| 5,144,068 A | 9/1992 | Smith et al. | |
| 5,220,058 A | 6/1993 | Fish et al. | |
| 5,227,520 A | 7/1993 | Cooper | |
| 5,227,524 A | 7/1993 | Jones | |
| 5,237,097 A | 8/1993 | Smith et al. | |
| 5,286,826 A | 2/1994 | Shih et al. | |
| 5,334,755 A | 8/1994 | Yoneda et al. | |
| 5,391,821 A | 2/1995 | Koyama et al. | |
| 5,416,237 A | 5/1995 | Aubigne et al. | |
| 5,466,874 A | 11/1995 | Scates et al. | |
| 5,625,095 A | 4/1997 | Miura et al. | |
| 5,653,853 A | 8/1997 | Kagotani et al. | |
| 5,672,744 A | 9/1997 | Kagotani et al. | |
| 5,683,492 A | 11/1997 | Hesse et al. | |
| 5,696,284 A | 12/1997 | Baker et al. | |
| 5,723,660 A | 3/1998 | Morimoto et al. | |
| 5,731,252 A | 3/1998 | Warner et al. | |
| 5,801,279 A | 9/1998 | Miura et al. | |
| 5,831,120 A | 11/1998 | Watson et al. | |
| 5,877,347 A | 3/1999 | Ditzel et al. | |
| 5,877,348 A | 3/1999 | Ditzel et al. | |
| 5,883,295 A | 3/1999 | Sunleu et al. | |
| 5,916,422 A | 6/1999 | Kimura et al. | |
| 5,932,764 A | 8/1999 | Morris et al. | |
| 5,942,460 A | 8/1999 | Garland et al. | |
| 5,962,735 A | 10/1999 | Kulprathipanja et al. | |
| 6,066,762 A | 5/2000 | Yoneda et al. | |
| 6,143,930 A | 11/2000 | Singh et al. | |
| 6,225,498 B1 | 5/2001 | Blay et al. | |
| 6,255,527 B1 | 7/2001 | Muskett | |
| 6,339,171 B1 | 1/2002 | Singh et al. | |
| 6,657,078 B2 | 12/2003 | Scates et al. | |
| 7,005,541 B2 | 2/2006 | Cheung et al. | |
| 7,208,624 B2 | 4/2007 | Scates et al. | |
| 7,223,883 B2 | 5/2007 | Picard et al. | |
| 7,223,886 B2 | 5/2007 | Scates et al. | |
| 7,271,293 B2 | 9/2007 | Trueba et al. | |
| 7,476,761 B2 | 1/2009 | Kojima | |
| 7,678,940 B2 | 3/2010 | Miura et al. | |
| 7,683,212 B2 | 3/2010 | Kojima et al. | |
| 7,838,701 B2 | 11/2010 | Trueba et al. | |
| 7,855,306 B2 | 12/2010 | Zinobile et al. | |
| 7,884,237 B2 | 2/2011 | Shaver | |
| 8,076,507 B2 | 12/2011 | Scates et al. | |
| 8,173,076 B2 | 5/2012 | Powell et al. | |
| 8,530,696 B2 | 9/2013 | Zinobile | |
| 8,697,908 B2 | 4/2014 | Torrence et al. | |
| 8,889,904 B2 | 11/2014 | Shaver et al. | |
| 8,940,932 B2 | 1/2015 | Shimizu | |
| 8,957,248 B2 | 2/2015 | Miura et al. | |
| 2006/0011462 A1 | 1/2006 | Horiguchi et al. | |
| 2006/0247466 A1 | 11/2006 | Zinobile et al. | |
| 2009/0036710 A1 | 2/2009 | Miura et al. | |
| 2009/0062525 A1 | 3/2009 | Shibata et al. | |
| 2009/0259072 A1 | 10/2009 | Umehara et al. | |
| 2011/0288333 A1 | 11/2011 | Shaver et al. | |
| 2012/0078012 A1 | 3/2012 | Torrence et al. | |
| 2012/0090981 A1 | 4/2012 | Torrence et al. | |
| 2012/0132515 A1 | 5/2012 | Ohno | |
| 2013/0026458 A1 | 1/2013 | Fukui et al. | |
| 2013/0116470 A1 | 5/2013 | Miura et al. | |
| 2013/0204014 A1 | 8/2013 | Nishihara et al. | |
| 2013/0261334 A1 | 10/2013 | Shimizu et al. | |
| 2013/0264186 A1 | 10/2013 | Shimizu et al. | |
| 2013/0281735 A1 | 10/2013 | Shimizu et al. | |
| 2013/0296616 A1* | 11/2013 | Hallinan | C07C 51/12 568/909 |
| 2015/0025270 A1 | 1/2015 | Shimizu et al. | |

FOREIGN PATENT DOCUMENTS

| | | |
|---|---|---|
| CN | 101053841 A | 10/2007 |
| EP | 0161874 A1 | 11/1985 |
| EP | 0685445 A1 | 12/1995 |
| EP | 1737808 B1 | 11/2006 |
| JP | 2000-72712 A | 3/2000 |
| WO | 9822420 A1 | 5/1998 |
| WO | 0216297 A1 | 2/2002 |
| WO | 2005085166 A1 | 9/2005 |

OTHER PUBLICATIONS

Akinori, S. "Acetic Acid Synthesis From Methanol" J. Japan Petroleum Institute 20(5); 379-462 (1977).
English translation of JP2000-72712.
English translation of Akinori, S. "Acetic Acid Synthesis From Methanol" J. Japan Petroleum Institute 20(5); 379-462 (1977).

* cited by examiner

PROCESS TO CONTROL HI CONCENTRATION IN RESIDUUM STREAM

RELATED APPLICATIONS

This application is a continuation-in-part of copending U.S. Ser. No. 14/724,197, filed May 28, 2015, which claims priority benefit to U.S. Provisional Application No. 62/112,120, filed Feb. 4, 2015, the disclosures of which are fully incorporated herein by reference.

BACKGROUND

Acetic acid production by carbonylation includes continuously reacting methanol and carbon monoxide in the presence of a catalyst in a reactor. The reaction mixture present in the reactor comprises a transition metal, which may be a Group VIII metal, which may be iridium and/or rhodium or nickel, and may further include one or more solvents, water, various stabilizers, co-catalysts, promoters, and the like. Reaction mixtures known in the art may comprise acetic acid, methyl acetate, methyl iodide, hydrogen iodide, a hydrogen iodide promoter, and the like.

A complex network of inter-dependent equilibria involving liquid acetic acid reaction components exists within the reaction mixture present in the reactor, which include those directed to the formation of acetic acid, as well as those directed to the formation of various impurities which are also produced in the reactor. Impurities which may be present in acetic acid include permanganate reducing compounds (PRCs) such as acetaldehyde.

Hydrogen iodide, HI, whether present in molecular form as hydrogen iodide or dissociated in a solvent as hydriodic acid, is present in the reaction mixture according to various production schemes. However, HI is highly corrosive to metals and presents various challenges in acetic acid production.

Attempts in the art are directed to minimizing HI outside of the reactor, with the ultimate goal of eliminating it outside of the reactor. Examples include processes directed to injecting methanol into a distillation column with the purported intention of reacting the methanol with the HI present therein to form methyl iodide and water. (cf. JP2000-72712, Japanese application 10-244590, filed Aug. 31, 1998, the entire contents and disclosure of which is hereby incorporated by reference). However, processes directed to minimizing HI to reduce or eliminate corrosion issues failed to realize benefits associated with particular concentrations of HI outside the reactor. There is a need to control HI concentrations within particular ranges in various aspects of an acetic acid production process.

SUMMARY

In embodiments according to the instant disclosure, methods to produce acetic acid comprise processes wherein the densities of the streams are controlled to ensure separation of phases critical to removal of acetaldehyde and other contaminates. In embodiments, HI may be produced and controlled above a minimum concentration and/or within a selected concentration range above the minimum concentration in one or more streams outside of the carbonylation reactor. In embodiments, this HI allows for formation of dimethyl ether within the purification processes disclosed, which facilitates phase separation and reduces the amount of methyl iodide lost as waste. In particular, the densities of the various distillation streams are controlled during distillation of a stream within an aldehyde removal process.

In embodiments, a process comprises providing a feed stream having a first density comprising water, acetic acid, methyl acetate, at least one PRC, and greater than about 30 wt % methyl iodide to a distillation column comprising a distillation zone and a bottom sump zone; and distilling the feed stream at a pressure and a temperature sufficient to produce an overhead stream having a second density and comprising greater than about 40 wt % methyl iodide and at least one PRC; wherein a percent decrease between the first density and the second density is from 20% to 35%.

In embodiments, a process comprises the steps of:
a. carbonylating a reaction medium comprising a reactant feed stream comprising methanol, methyl acetate, dimethyl ether, or mixtures thereof, water, a rhodium catalyst, an iodide salt and methyl iodide in a reactor to form acetic acid;
b. distilling a stream derived from the reaction medium in a first column to yield an acetic acid side stream which is further purified to produce a product acetic acid stream, and a first overhead stream comprising methyl iodide, water, acetic acid, methyl acetate, and at least one PRC;
c. biphasically separating the first overhead stream into a light phase comprising methyl iodide, acetic acid, methyl acetate, at least one PRC, and greater than about 30 wt % water, and a heavy phase comprising water, acetic acid, methyl acetate, at least one PRC, and greater than about 30 wt % methyl iodide;
d. directing a second column feed stream comprising or derived from the heavy phase into a second distillation column comprising a distillation zone and a bottom sump zone;
e. distilling the second column feed stream at a pressure and a temperature sufficient to produce a second overhead stream having a second density and which comprises greater than about 40 wt % methyl iodide and at least one PRC, and a residuum stream flowing from the bottom sump zone having a third density which is less than the first density, and which comprises greater than about 0.1 wt % water, wherein a percent decrease between the first density and the second density is from 20% to 35%;
f. extracting at least a portion of the second column overhead stream comprising methyl iodide and at least one PRC with water to produce an aqueous stream comprising the at least one PRC, and a raffinate stream having a fourth density which is greater than the first density, and which comprises greater than about 90 wt % methyl iodide; and
g. directing at least a first portion of the raffinate stream back into the distillation zone of the second distillation column.

This summary is provided to introduce a selection of concepts that are further described below in the detailed description. This summary is not intended to identify key or essential features of the claimed subject matter, nor is it intended to be used as an aid in limiting the scope of the claimed subject matter.

DETAILED DESCRIPTION

Figure 1:
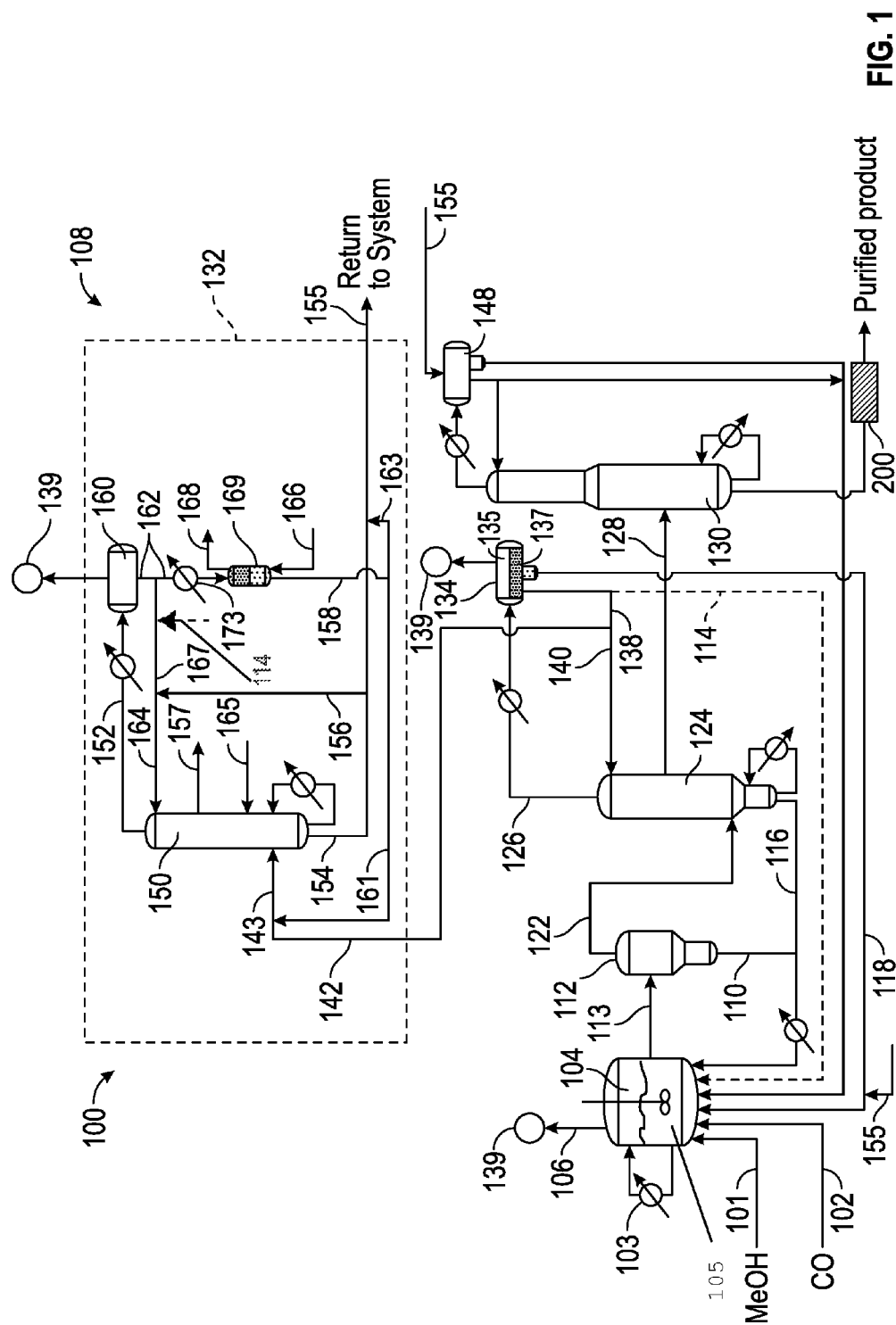
FIG. 1 is a schematic diagram of a process to produce acetic acid according to an embodiment.

At the outset, it should be noted that in the development of any such actual embodiment, numerous implementation-specific decisions must be made to achieve the developer's specific goals, such as compliance with system related and business related constraints, which will vary from one implementation to another. In addition, the processes disclosed herein can also comprise components other than those cited or specifically referred to, as is apparent to one having average or reasonable skill in the art.

In the summary and this detailed description, each numerical value should be read once as modified by the term "about" (unless already expressly so modified), and then read again as not so modified unless otherwise indicated in context. Also, in the summary and this detailed description, it should be understood that a concentration range listed or described as being useful, suitable, or the like, is intended that any and every concentration within the range, including the end points, is to be considered as having been stated. For example, "a range of from 1 to 10" is to be read as indicating each and every possible number along the continuum between about 1 and about 10. Thus, even if specific data points within the range, or even no data points within the range, are explicitly identified or refer to only a few specific data points, it is to be understood that inventors appreciate and understand that any and all data points within the range are to be considered to have been specified, and that inventors possessed knowledge of the entire range and all points within the range.

Throughout the entire specification, including the claims, the following terms have the indicated meanings unless otherwise specified.

As used in the specification and claims, "near" is inclusive of "at." The term "and/or" refers to both the inclusive "and" case and the exclusive "or" case, and is used herein for brevity. For example, a mixture comprising acetic acid and/or methyl acetate may comprise acetic acid alone, methyl acetate alone, or both acetic acid and methyl acetate.

All percentages are expressed as weight percent (wt %), based on the total weight of the particular stream or composition present, unless otherwise noted. Room temperature is 25° C. and atmospheric pressure is 101.325 kPa unless otherwise noted.

For purposes herein:
acetic acid may be abbreviated as "AcOH";
acetaldehyde may be abbreviated as "AcH";
methyl acetate may be abbreviated "MeAc";
methanol may be abbreviated "MeOH";
methyl iodide may be abbreviated as "MeI";
carbon monoxide may be abbreviated "CO"; and
dimethyl ether may be abbreviated "DME".

HI refers to either molecular hydrogen iodide or dissociated hydriodic acid when at least partially ionized in a polar medium, typically a medium comprising at least some water. Unless otherwise specified, the two are referred to interchangeably. Unless otherwise specified, HI concentration is determined via acid-base titration using a potentiometric end point. In particular, HI concentration is determined via titration with a standard lithium acetate solution to a potentiometric end point. It is to be understood that for purposes herein, the concentration of HI is not determined by subtracting a concentration of iodide assumed to be associated with a measurement of corrosion metals or other non H+ cations from the total ionic iodide present in a sample.

It is to be understood that HI concentration does not refer to iodide ion concentration. HI concentration specifically refers to HI concentration as determined via potentiometric titration.

This subtraction method is an unreliable and imprecise method to determine relatively lower HI concentrations (i.e., less than about 5 weight percent) due to the fact that it assumes all non-H+ cations (such as cations of Fe, Ni, Cr, Mo) are associated with iodide anion exclusively. In reality, a significant portion of the metal cations in this process can be associated with acetate anion. Additionally, many of these metal cations have multiple valence states, which adds even more unreliability to the assumption on the amount of iodide anion which could be associated with these metals. Ultimately, this method gives rise to an unreliable determination of the actual HI concentration, especially in view of the ability to perform a simple titration directly representative of the HI concentration.

For purposes herein, an "overhead" of a distillation column refers to at least one of the lower boiling condensable fractions which exits at or near the top, (e.g., proximate to the top), of the distillation column, and/or the condensed form of that stream or composition. Obviously, all fractions are ultimately condensable, yet for purposes herein, a condensable fraction is condensable under the conditions present in the process as readily understood by one of skill in the art. Examples of non-condensable fractions may include nitrogen, hydrogen, and the like. Likewise, an overhead stream may be taken just below the upper most exit of a distillation column, for example, wherein the lowest boiling fraction is a non-condensable stream or represents a de-minimis stream, as would be readily understood by one of reasonable skill in the art.

The residuum of a distillation column refers to one or more of the highest boiling fractions which exit at or near the bottom of the distillation column, also referred to herein as flowing from the bottom sump of the column. It is to be understood that a residuum may be taken from just above the very bottom exit of a distillation column, for example, wherein the very bottom fraction produced by the column is a salt, an unusable tar, a solid waste product, or a de-minimis stream as would be readily understood by one of reasonable skill in the art.

For purposes herein, distillation columns comprise a distillation zone and a bottom sump zone. The distillation zone includes everything above the bottom sump zone, i.e., between the bottom sump zone and the top of the column. For purposes herein, the bottom sump zone refers to the lower portion of the distillation column in which a liquid reservoir of the higher boiling components is present (e.g., the bottom of a distillation column) from which the bottom or residuum stream flows upon exiting the column. The bottom sump zone may include reboilers, control equipment, and the like.

It is to be understood that the term "passages", "flow paths", "flow conduits", and the like in relation to internal components of a distillation column are used interchangeably to refer to holes, tubes, channels, slits, drains, and the like, which are disposed through and/or which provide a path for liquid and/or vapor to move from one side of the internal component to the other side of the internal component. Examples of passages disposed through a structure such as a liquid distributor of a distillation column include drain holes, drain tubes, drain slits, and the like, which allow a liquid to flow through the structure from one side to another.

Average residence time is defined as the sum total of all liquid volume hold-up for a given phase within a distillation zone divided by the average flow rate of that phase through the distillation zone. The hold-up volume for a given phase can include liquid volume contained in the various internal components of the column including collectors, distributors and the like, as well as liquid contained on trays, within downcomers, and/or within structured or random packed bed sections.

The average total residence time of the feed stream in the distillation zone of the column is necessarily less than (and does not refer to) the total residence time of the feed stream within the distillation column. The total residence time of a stream in a distillation column is the sum of both the total residence time of the feed stream in the distillation zone and the total residence time of the feed stream in the bottom sump zone of the column.

As used herein, internal components located within a distillation zone of a column include packing sections, liquid distributors, liquid collectors, liquid redistributors, trays, supports, and the like.

As used herein, mass flow rate refers to kg/hr unless otherwise stated, and may be determined directly or calculated from volumetric measurements.

As used herein, a carbonylatable reactant is any material which reacts with carbon monoxide under reaction conditions to produce acetic acid, or the intended product. Carbonylatable reactants include methanol, methyl acetate, dimethyl ether, methyl formate, and the like.

As used herein, when at least a portion of a stream or other composition is further processed, such as by being recycled or directed back into another portion of the process, it is to be understood that a "portion" refers to an aliquot of the stream or composition. Stated another way, a "portion" refers to a portion of the entire mass flow of the stream or a portion of the entire composition. It is to be expressly understood that a "portion" of a stream or composition does not refer to selective components present therein. Accordingly, recycle of a portion of stream does not include any process in which components in the stream at the origination point are not present at the disposition point.

When a portion of a stream or composition is directly recycled or otherwise directed to a disposition point, the mass of each component originally present in the stream is present at the disposition point at the same relative proportions.

A portion of a stream or composition which is indirectly recycled or otherwise directed may be combined with other streams, yet the absolute mass of each and every component present in the original stream is still present at the disposition point, and the changes to the overall composition are the result of combining the particular stream with others.

As used herein, a stream or composition "derived" from another stream may include the entire stream or may include less than all of the individual components initially present in the stream. Accordingly, recycle of a stream derived from another stream does not necessarily require the mass of each component originally present in the stream to be present at the disposition point. A stream or composition "derived" from a particular stream may thus include a stream which is subject to further processing or purification prior to disposition. For example, a stream which is distilled prior to being recycled to a final disposition point is derived from the original stream.

For purposes herein, permanganate reducing compounds (PRCs) include acetaldehyde, acetone, methyl ethyl ketone, butyraldehyde, crotonaldehyde, 2-ethyl crotonaldehyde, 2-ethyl butyraldehyde, and the like, and the aldol and cross aldol condensation products thereof.

For purposes herein, density is determined on a stream at the average temperature of the particular stream under process conditions, unless otherwise indicated. Accordingly, if a first stream is supplied to a distillation column at an average temperature of 60° C., and the second stream produced from that distillation column is produced at an average temperature of 50° C., for purposes herein including determining relative increases and decreases between densities of the two stream, the density of the first stream is determined at 60° C. (the corresponding average process temperature of the particular stream) and the density of the second stream is determined at 50° C. (the corresponding average process temperature of the particular stream). For purposes herein, a percent decrease between a first density and a second density is determined according to equation I:

(first density−second density)/first density*100%     (I)

For purposes herein, a percent increase between a first density and a second density is the absolute value of the value determined by equation (I); i.e., since an increase in density from the first density to the second density will produce a negative number according to equation (I), the absolute valve of the negative result obtained is reported.

HI has physical properties which are generally considered detrimental to various process components typically present in commercial acetic acid processes due to corrosion issues. In particular, the presence of HI in distillation columns is considered detrimental, especially to heat exchange surfaces such as reboilers and the like. While HI is necessarily present within the carbonylation reactor utilized in the production of acetic acid via the "Monsanto" and AO® Technology processes, numerous applications in the art are directed to reducing and/or eliminating the presence of HI in streams found outside of the carbonylation reactor.

However, it has been discovered that when HI is present at particular concentrations within one or more streams outside of the carbonylation reactor of an acetic acid process, one or more previously unknown benefits are realized. For example, it has been suggested that HI is instrumental in the formation of dimethyl ether (DME) under conditions present within a distillation column of an aldehyde removal system (ARS) according to the equilibrium equations:

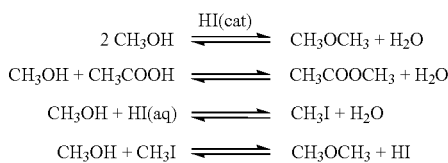

This dimethyl ether unexpectedly functions to lower the concentration of methyl iodide in the aqueous waste streams produced by such aldehyde removal systems as disclosed in U.S. Pat. No. 7,223,883, U.S. Pat. No. 7,223,886, and U.S. Pat. No. 8,076,507, and the like, all of which are incorporated by reference herein. Accordingly, prior art disclosures directed to eliminating HI outside of the reactor fail to realize the benefits which flow from HI concentrations according to embodiments disclosed herein. Embodiments disclosed herein further provide methods by which the formation of HI within the distillation column of the aldehyde removal system, and the concentration of HI within the sump of this distillation column may be controlled. By controlling the HI concentration in the sump of the ARS distillation column, the amount of DME produced in the column may be controlled to obtain the benefits which flow therefrom.

In embodiments, a process comprises providing a feed stream having a first density comprising water, acetic acid, methyl acetate, at least one PRC, and greater than about 30 wt % methyl iodide to a distillation column comprising a distillation zone and a bottom sump zone; and distilling the feed stream at a pressure and a temperature sufficient to produce an overhead stream having a second density and comprising greater than about 40 wt % methyl iodide and at least one PRC, wherein a percent decrease between the first density and the second density at 50° C. is from 20% to 35%.

The process of claim 1, wherein the specific gravity of the second density relative to water is from 1.15 to 1.6 at 50° C.

In embodiments, a residuum stream flowing from the bottom sump zone has a third density which is less than the first density, and comprises greater than about 0.1 wt % water. In embodiments, the residuum stream comprises greater than or equal to about 0.11 wt % HI.

In embodiments, a percent decrease between the first density and the third density is from 5% to 10%.

In embodiments, distillation of the feed stream produces a first liquid phase comprising greater than about 50 weight percent water and a second liquid phase comprising greater than about 50 weight percent methyl iodide within the distillation zone, and wherein the distillation zone comprises a plurality of internal components, each having a component liquid retention volume, wherein each of the internal components is dimensioned and arranged such that an average residence time of the first liquid phase and an average residence time of the second liquid phase in each of the component liquid retention volumes is less than about 30 minutes. In embodiments, at least one internal component is dimensioned and arranged such that the average residence time of the second liquid phase is greater than or equal to the average residence time of the first liquid phase in the corresponding component liquid retention volume.

In embodiments, the process further comprises directing a top flush stream comprising water into the distillation zone at a mass flow rate which is greater than or equal to about 0.1 percent of the mass flow rate of the feed stream. In embodiments, the top flush stream comprises a portion of the bottom residuum stream.

In embodiments, the process further comprises directing a bottom flush stream comprising acetic acid, water, or both into the bottom sump zone at a mass flow rate which is greater than or equal to about 0.1 percent of the mass flow rate of the feed stream. In embodiments, the overhead stream comprises dimethyl ether. In embodiments, the concentration of dimethyl ether in overhead stream is from 0.1 wt % to 50 wt %, based on the total amount of the overhead stream present.

In embodiments, a process comprises the steps of carbonylating a reaction medium comprising a reactant feed stream comprising methanol, methyl acetate, dimethyl ether, or mixtures thereof, water, a rhodium catalyst, an iodide salt and methyl iodide to form acetic acid; distilling a stream derived from the reaction medium in a first column to yield an acetic acid side stream which is further purified to produce a product acetic acid stream, and a first overhead stream comprising methyl iodide, water, acetic acid, methyl acetate, and at least one PRC; biphasically separating the first overhead stream into a light phase comprising methyl iodide, acetic acid, methyl acetate, at least one PRC, and greater than about 30 wt % water, and a heavy phase comprising water, acetic acid, methyl acetate, at least one PRC, and greater than about 30 wt % methyl iodide; directing a second column feed stream comprising or derived from the heavy phase into a second distillation column comprising a distillation zone and a bottom sump zone; distilling the second column feed stream at a pressure and a temperature sufficient to produce a second overhead stream having a second density and comprising greater than about 40 wt % methyl iodide and at least one PRC, and a residuum stream flowing from the bottom sump zone having a third density which is less than the first density, comprising greater than about 0.1 wt % water, wherein a percent decrease between the first density and the second density is from 20% to 35%; extracting at least a portion of the second column overhead stream comprising methyl iodide and at least one PRC with water to produce an aqueous waste stream comprising the at least one PRC, and a raffinate stream comprising greater than about 90 wt % methyl iodide having a fourth density which is greater than the first density; and directing at least a first portion of the raffinate stream back into the distillation zone of the second distillation column.

In embodiments, the specific gravity of the second density relative to water is from 1.15 to 1.6 at 50° C. In embodiments, a percent increase between the first density and the fourth density is from 10% to 20%. In embodiments, the process further comprises directing a top flush stream comprising water into the distillation zone of the second distillation column at a mass flow rate of greater than or equal to about 0.1 percent of the mass flow rate of the second column feed stream, wherein the top flush stream comprises a portion of the bottom residuum stream, at least a portion of the first portion of the raffinate stream, a portion of the light phase separated from the first overhead stream, or a combination thereof.

In embodiments, the process further comprises directing a bottom flush stream comprising acetic acid, water, or both into the bottom sump zone of the second distillation column at a mass flow rate of greater than or equal to about 0.1 percent of the mass flow rate of the second column feed stream.

In embodiments, the second column overhead stream comprises dimethyl ether. In embodiments, the process further comprises directing a second portion of the raffinate stream comprising methyl iodide and dimethyl ether back into the reaction medium. In embodiments, a mass flow rate of the first portion of the raffinate stream is greater than or equal to a mass flow rate of the second portion of the raffinate stream. In embodiments, a bottom temperature of the second distillation column is about 70° C. to about 100° C., a top temperature of the second distillation column is about 40° C. to about 60° C., a pressure of the second distillation column is from atmospheric pressure to about 700 kPa above atmospheric pressure, or a combination thereof.

Acetic Acid Production System

Processes to produce acetic acid via methanol carbonylation can be conveniently divided into three main areas: the reaction systems, the internal purification systems, and the product purification systems.

The reaction systems include the carbonylation reactor, the flasher, and the like. The internal purification systems include the light ends recovery/acetic acid product separation systems, aldehyde removal systems, and the like.

The product purification systems include drying columns, resin beds, and the like, directed to purifying the acetic acid to produce the final product.

Examples of processes suitable to produce the distillation column feed stream according to the instant disclosure include those described in U.S. Pat. No. 3,769,329; U.S. Pat. No. 3,772,156; U.S. Pat. No. 4,039,395; U.S. Pat. No. 4,255,591; U.S. Pat. No. 4,615,806; U.S. Pat. No. 5,001,259; U.S. Pat. No. 5,026,908; U.S. Pat. No. 5,144,068; U.S. Pat. No. 5,237,097; U.S. Pat. No. 5,334,755; U.S. Pat. No. 5,625,095; U.S. Pat. No. 5,653,853; U.S. Pat. No. 5,683,492; U.S. Pat. No. 5,831,120, U.S. Pat. No. 5,227,520; U.S. Pat. No. 5,416,237, U.S. Pat. No. 5,731,252; U.S. Pat. No. 5,916,422; U.S. Pat. No. 6,143,930; U.S. Pat. No. 6,225,498, U.S. Pat. No. 6,255,527; U.S. Pat. No. 6,339,171; U.S. Pat. No. 6,657,078; U.S. Pat. No. 7,208,624; U.S. Pat. No. 7,223,883; U.S. Pat. No. 7,223,886; U.S. Pat. No. 7,271,293; U.S. Pat. No. 7,476,761; U.S. Pat. No. 7,838,701; U.S. Pat. No. 7,855,306; U.S. Pat. No. 8,076,507; US20060247466; US20090036710; US20090259072; US20090062525; US20110288333; US20120090981; US20120078012; US20130116470; US20130261334; US20130264186; US20130281735; US20130261334; US20130281735; EP0161874; WO9822420; WO0216297; WO2013137236, and the like, the entire contents and disclosure of which are hereby incorporated by reference.

Reaction Systems and Processes

As shown in FIG. 1, the processes 100 includes directing a methanol-containing feed stream 101 and a carbon monoxide-containing feed stream 102 into a liquid phase reaction medium 105 of a carbonylation reactor 104, wherein they are contacted in the presence of catalyst, water, methyl iodide, methyl acetate, acetic acid, an iodide salt, HI, and other reaction medium components to produce acetic acid.

A portion of the reaction medium 105 is continuously removed from the reactor 104 to the flasher 112 via line 113. This stream is subject to flash or low pressure distillation in flasher 112, wherein acetic acid and other volatile components are separated from the non-volatile components present in the reaction medium. The non-volatile components are recycled back into the reaction medium via stream 110. The volatile components of the reaction medium are directed overhead via line 122 into the light ends column 124.

As the figure shows, the process includes a number of recycle lines through which various streams are recycled back into the reaction medium from other parts of the process. The process also includes various vapor purge lines, and the like. It is to be understood that all vents and other vapor lines are connected to one or more scrubber or vent systems and that all condensable components discharged to the scrubber system are eventually recycled back into the carbonylation reactor.

In embodiments, the reaction medium comprises a metal catalyst, or a Group VIII metal catalyst, or a catalyst comprising rhodium, nickel and/or iridium. In embodiments, the reaction medium comprises a rhodium catalyst, typically from about 200 to about 5000 parts per million (ppm) by weight, based on the total weight of the reaction medium.

In embodiments, the reaction medium further comprises a halogen-containing catalyst promoter, typically methyl iodide (MeI). In embodiments, the reaction medium comprises greater than or equal to about 5 weight percent MeI, or from about 5 weight percent to about 50 weight percent MeI. In embodiments, the reaction medium comprises greater than or equal to about 50 weight percent AcOH.

In embodiments, the reaction medium comprises a finite concentration of water. In so-called low-water processes, the reaction medium comprises a finite concentration of water up to about 14 wt %.

In embodiments, the reaction medium has a finite water concentration. In embodiments, the water concentration in the reaction medium is greater than or equal to 0.1 wt %, or 0.5 wt %, or 1 wt %, or 2 wt %, or 3.5 wt %, or 4 wt %, or 5 wt %, and less than or equal to 10 wt %, 7 wt %, or 6 wt %. In embodiments, the reactor water concentration is from 0.1 to 5 wt %, or 0.2 to 4 wt %, or 1 to 3 wt %, based on the total amount of the reaction medium present.

In embodiments, the reaction medium further comprises from about 0.5 weight percent to less than 20 weight percent methyl acetate (MeAc).

In embodiments, the reaction medium further comprises hydrogen iodide and one or more iodide salts, typically lithium iodide (LiI), in an amount sufficient to produce a total iodide ion concentration greater than or equal to about 2 weight percent and less than or equal to about 30 weight percent of the reaction medium.

In embodiments, the reaction medium may further comprise hydrogen, determined according to a hydrogen partial pressure present in the reactor. In embodiments, the partial pressure of hydrogen in the reactor is greater than or equal to about 0.7 kPa (0.1 psia), or 3.5 kPa (0.5 psia), or 6.9 kPa (1 psia), and less than or equal to about 1.03 MPa (150 psia), or 689 kPa (100 psia), or 345 kPa (50 psia), or 138 kPa (20 psia).

In embodiments, the reactor temperature i.e., the temperature of the reaction medium, is greater than or equal to about 150° C. In embodiments, the reactor temperature is greater than or equal to about 150° C. and less than or equal to about 250° C. In embodiments, the reactor temperature is greater than or equal to about 180° and less than or equal to about 220° C.

In embodiments, the carbon monoxide partial pressure in the reactor is greater than or equal to about 200 kPa. In embodiments, the CO partial pressure is greater than or equal to about 200 kPa and less than or equal to about 3 MPa. In embodiments, the CO partial pressure in the reactor is greater than or equal to about the 300 kPa, or 400 kPa, or 500 kPa and less than or equal to about 2 MPa, or 1 MPa. The total reactor pressure represents the combined partial pressure of all reactants, products, and by-products present therein. In embodiments, the total reactor pressure is greater than or equal to about 1 MPa and less than or equal to about 4 MPa.

In an embodiment, vapor product stream 122 from flasher 112 comprises acetic acid, methyl iodide, methyl acetate, water, acetaldehyde, and hydrogen iodide. In one embodiment, vapor product stream 122 comprises acetic acid in an amount from 45 to 75 wt. %, methyl iodide in an amount from 20 to 50 wt. %, methyl acetate in an amount of less than or equal to 9 wt. %, and water in an amount of less than or equal to 15 wt. %, based on the total weight of the vapor product stream. In another embodiment, vapor product stream 122 comprises acetic acid in an amount from 45 to 75 wt. %, methyl iodide in an amount from 24 to less than 36 wt. %, methyl acetate in an amount of less than or equal to 9 wt. %, and water in an amount of less than or equal to 15 wt. %, based on the total weight of the vapor product stream. In embodiments, vapor product stream 122 comprises acetic acid in an amount from 55 to 75 wt. %, methyl iodide in an amount from 24 to 35 wt. %, methyl acetate in an amount from 0.5 to 8 wt. %, and water in an amount from 0.5 to 14 wt. %. In still other embodiments, vapor product stream 122 comprises acetic acid in an amount from 60 to 70 wt. %, methyl iodide in an amount from 25 to 35 wt. %, methyl acetate in an amount from 0.5 to 6.5 wt. %, and water in an amount from 1 to 8 wt. %. The acetaldehyde concentration in the vapor product stream may be in an amount from 0.005 to 1 wt. %, based on the total weight of the vapor product stream, e.g., from 0.01 to 0.8 wt. %, or from 0.01 to 0.7 wt. %. In some embodiments the acetaldehyde may be present in amounts less than or equal to 0.01 wt. %. Vapor product stream 122 may comprise hydrogen iodide in an amount less than or equal to 1 wt. %, based on the total weight of the vapor product stream, or less than or equal to 0.5 wt. %, or less than or equal to 0.1 wt. %. Vapor product stream 122 may be substantially free of, i.e., contains less than or equal to 0.0001 wt. %, propionic acid, based on the total weight of the vapor product stream.

Liquid recycle stream 110 comprises acetic acid, the metal catalyst, corrosion metals, as well as other various compounds. In an embodiment, liquid recycle stream 110 comprises acetic acid in an amount from 60 to 90 wt. %, metal catalyst in an amount from 0.01 to 0.5 wt. %; corrosion metals (e.g., nickel, iron and chromium) in a total amount from 10 to 2500 wppm; lithium iodide in an amount from 5 to 20 wt. %; methyl iodide in an amount from 0.5 to 5 wt. %; methyl acetate in an amount from 0.1 to 5 wt. %; water in an amount from 0.1 to 8 wt. %; acetaldehyde in an amount of less than or equal to 1 wt. % (e.g., from 0.0001 to 1 wt. % acetaldehyde); and hydrogen iodide in an amount of less than or equal to 0.5 wt. % (e.g., from 0.0001 to 0.5 wt. % hydrogen iodide).

Light Ends Recovery/Acetic Acid Product Separation Systems and Processes

In embodiments, the overhead stream from flasher 112 is directed as stream 122 to a first distillation column 124, which may also be referred to as the light ends column or the stripper column. Accordingly, the feed stream to the first distillation column is derived from the reaction medium because it undergoes distillation prior to entering the first distillation column. Distillation of the feed stream in the light ends column 124 yields a low-boiling first overhead vapor stream 126, referred to herein as the first overhead stream 126, and a purified acetic acid stream 128. Stream 128 is a crude acetic acid stream, which is subsequently purified. In embodiments, acetic acid stream 128 is removed as a side stream. The light ends column 124 further produces a high boiling residuum stream 116, which may be subject to further purification and/or may be recycled back into the reaction medium.

Each distillation column utilized in the process may be a conventional distillation column, e.g., a plate column, a packed column, and others. Plate columns may include a perforated plate column, bubble-cap column, Kittel tray column, uniflux tray, or a ripple tray column. The material of the distillation column is not limited and may include a glass, a metal, a ceramic, or other suitable material can be used. For a plate column, the theoretical number of plates is not particularly limited and depending on the species of the component to be separate, may depend on the component to be separated, and may include up to 50 80 plates, e.g., from 2 to 80, from 5 to 60, from 5 to 50, or more preferably from 7 to 35. The distillation column may include a combination of different distillation apparatuses. For example, a combination of bubble-cap column and perforated plate column may be used as well as a combination of perforated plate column and a packed column.

The distillation temperature and pressure in the distillation system can suitably be selected depending on the condition such as the species of the objective carboxylic acid and the species of the distillation column, or the removal target selected from the lower boiling point impurity and the higher boiling point impurity according to the composition of the feed stream. For example, in a case where the purification of acetic acid is carried out by the distillation column, the inner pressure of the distillation column (usually, the pressure of the column top) may be from 0.01 to 1 MPa, e.g., from 0.02 to 0.7 MPa, and more preferably from 0.05 to 0.5 MPa in terms of gauge pressure. Moreover, the distillation temperature for the distillation column, namely the inner temperature of the column at the temperature of the column top, can be controlled by adjusting the inner pressure of the column, and, for example, may be from 20 to 200° C., e.g., from 50 to 180° C., and more preferably about 100 to 160° C.

The material of each member or unit associated with the distillation system, including the columns, valves, condensers, receivers, pumps, reboilers, and internals, and various lines, each communicating to the distillation system may be suitable material such as glass, metal, ceramic, or combinations thereof, and is not particularly limited to a specific one. In embodiments, the material of the foregoing distillation system and various lines are a transition metal or a transition-metal-based alloy such as iron alloy, e.g., a stainless steel, nickel or nickel alloy, zirconium or zirconium alloy thereof, titanium or titanium alloy thereof, or aluminum alloy. Suitable iron-based alloy include any alloy containing iron as a main component, e.g., a stainless steel that also comprises chromium, nickel, molybdenum and others. Suitable a nickel-based alloy include containing nickel as a main component and one or more of chromium, iron, cobalt, molybdenum, tungsten, manganese, and others, e.g., HASTELLOY™ and INCONEL™ Corrosion-resistant metals may be particularly suitable as materials for the distillation system and various lines.

In embodiments, acetic acid stream 128 is subjected to further purification in the product purification section of the process, such as in a drying column 130 to remove water to produce a final product acetic acid stream. In embodiments, the acetic acid stream 128 may be further purified in a heavy ends column (cf. WO0216297), and/or contacted with one or more absorbent, adsorbent, or purification resins in guard column 200 to remove various impurities (cf. U.S. Pat. No. 6,657,078) to produce a purified product acetic acid stream, indicated in FIG. 1 as the purified product.

In embodiments, the first overhead 126 is condensed and then directed into an overhead phase separation unit 134, (overhead decanter 134). The first overhead 126 comprises methyl iodide, methyl acetate, acetic acid, water, and at least one PRC. In embodiments, the condensed first overhead stream 126 is separated into a light aqueous phase 135 comprising greater than about 30 wt % water, or 40 wt % water, or 50 wt % water, acetic acid, methyl iodide, methyl acetate, and at least one PRC; and a heavy phase 137 comprising greater than about 30 wt % methyl iodide, or 40 wt % methyl iodide, or 50 wt % methyl iodide, methyl acetate, and at least one PRC. In view of the solubility of methyl iodide in water and vice-versa, the heavy phase 137 comprises some water and the light phase 135 comprises some methyl iodide.

The exact compositions of these two streams are a function of the methyl acetate, acetic acid, acetaldehyde, and other components which are also present in the light ends overhead stream 126. Although the specific compositions of light liquid phase 135 may vary widely, some exemplary compositions are provided below in Table 1.

TABLE 1

Exemplary Light Liquid Phase from Light Ends Overhead

| Component | conc. (Wt. %) | conc. (Wt. %) | conc. (Wt. %) |
|---|---|---|---|
| Water | 40-80 | 50-75 | 70-75 |
| Methyl Acetate | 1-50 | 1-25 | 1-15 |
| Acetic Acid | 1-40 | 1-25 | 5-15 |
| PRC's | <5 | <3 | <1 |
| Methyl Iodide | <10 | <5 | <3 |

In an embodiment, overhead decanter 134 is arranged and constructed to maintain a low interface level to prevent an excess hold up of methyl iodide. Although the specific compositions of heavy liquid phase 137 may vary widely, some exemplary compositions are provided below in Table 2.

TABLE 2

Exemplary Heavy Liquid Phase from Light Ends Overhead

| Component | conc. (Wt. %) | conc. (Wt. %) | conc. (Wt. %) |
|---|---|---|---|
| Water | 0.01-2 | 0.05-1 | 0.1-0.9 |
| Methyl Acetate | 0.1-25 | 0.5-20 | 0.7-15 |
| Acetic Acid | 0.1-10 | 0.2-8 | 0.5-6 |
| PRC's | <5 | <3 | <1 |
| Methyl Iodide | 40-98 | 50-95 | 60-85 |

In embodiments, at least a portion of the heavy phase 137, the light phase 135, or both is returned to the reaction medium via line 114. In embodiments, essentially all of the light phase 135 is recirculated to the reactor and the heavy phase 137 is forwarded to the aldehyde removal process 108. For purposes herein, examples are directed to forwarding the heavy phase 137 to the aldehyde removal process 108. It is to be understood, however, that the light phase 135 in combination with the heavy phase 135 may be forwarded to the aldehyde removal process 108. In embodiments, a portion of the light phase 135, typically from about 5 to 40 volume percent may be directed to the aldehyde removal system 108 and the remainder recycled to the reaction medium. In embodiments, a portion of the light phase 135, typically from about 5 to 40 volume percent may be directed to the aldehyde removal system 108 along with essentially 100 volume percent of the heavy phase 137, and the remainder recycled to the reaction medium. In embodiments, at least a portion of the condensed first column overhead 138 is directed back into the light ends column 124 as reflux via stream 140.

In embodiments, a stream derived from the first column overhead 126, i.e. the heavy phase 137, the light phase 135, or a combination of the two streams is provided as a feed stream 142 to the aldehyde removal system 108, (the ARS). The feed stream 142 comprises methyl iodide, water, acetic acid, methyl acetate, and at least one PRC.

For purposes herein, directing a second column feed stream comprising or derived from the heavy phase into a second distillation column indicates that the greater than 50 wt % of the total proportion of both the light phase 135 and the heavy phase 137 present in the second column feed stream is, or is derived from, the heavy phase.

In embodiments, the feed stream 142 comprises at least 10 wt % light phase 135, or 20 wt % light phase 135, or 30 wt % light phase 135, or 40 wt % light phase 135, and/or feed stream 142 comprises at least 50 wt % heavy phase 137, or 60 wt % heavy phase 137, or 70 wt % heavy phase 137, or 80 wt % heavy phase 137 or 90 wt % heavy phase 137, or consists essentially of heavy phase 137, based on the total amount of both the heavy phase and the light phase present in the second column feed stream 142.

Accordingly, feed stream 142 comprises at least a portion of the first column overhead 126, and the total amount of the this first column overhead stream 126 present in feed stream 142 consists of a X % light phase 135 and Y % heavy phase 137, wherein X %+Y %=100%. For the purposes of this calculation it is to be understood that feed stream 142 may comprise additional components and/or streams other than the relative proportions of stream 126.

In embodiments, the aldehyde removal system comprises at least one distillation column 150. The distillation column 150 comprising a distillation zone 312 and a bottom sump zone 314 (cf. FIG. 3).

As shown in FIG. 1, the aldehyde removal system 108 may comprise a single distillation column 150. In FIG. 1, the single distillation column ARS embodiment is generally indicated as 132. In this embodiment, the ARS feed stream 142 is distilled in the second distillation column 150 to remove water, acetic acid methyl iodide and methyl acetate from the residuum 154, and to form a second overhead stream 152 comprising the PRC's (acetaldehyde) concentrated in methyl iodide.

Figure 2:
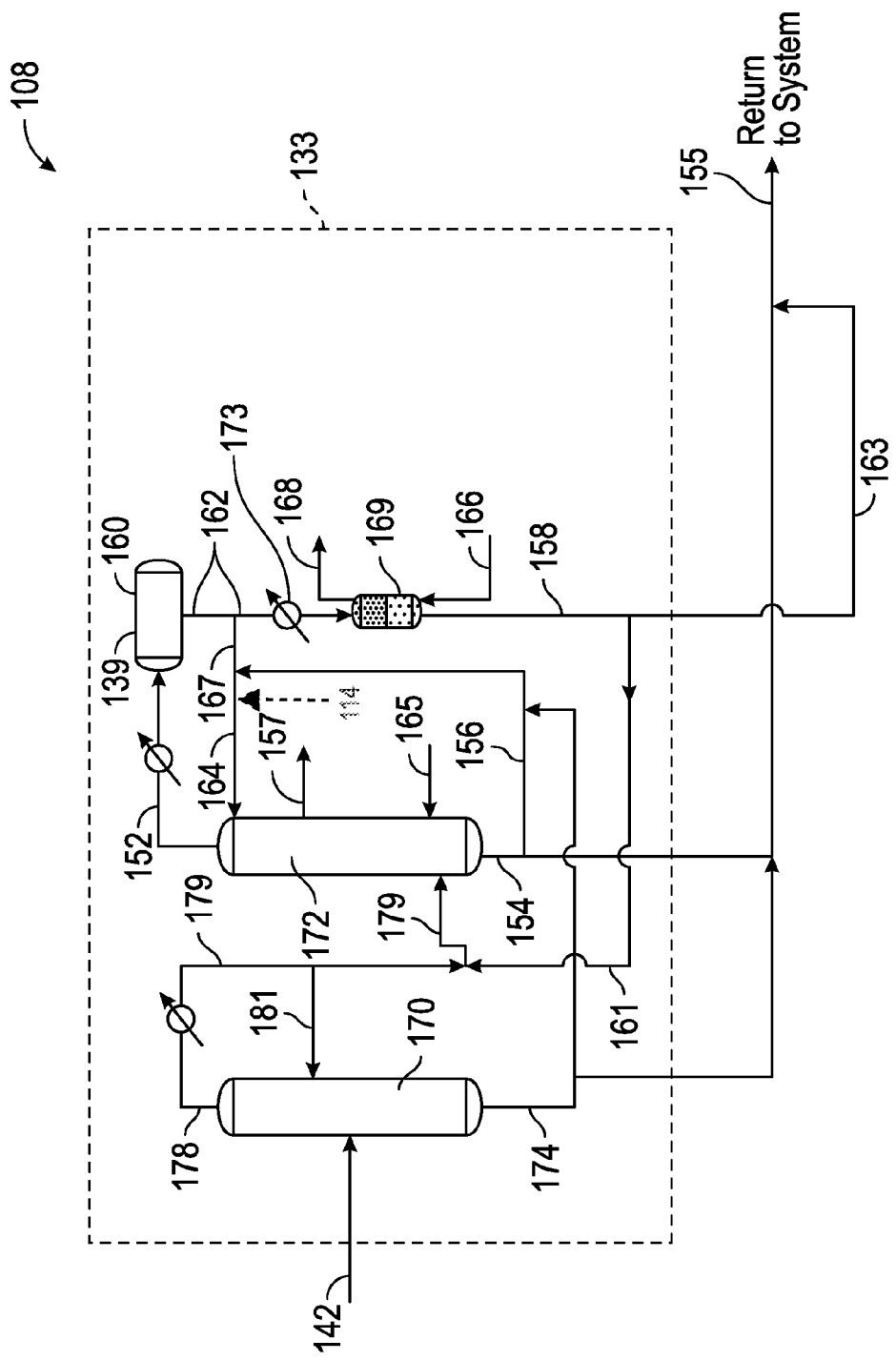
FIG. 2 is a schematic diagram of an alternative purification process according to an embodiment.

As shown in FIG. 2, in alternative embodiments, the aldehyde removal system 108 may comprise at least two distillation columns 170 and 172. This multi-column ARS is generally indicated as 133. In assembly 133, the feed stream 142 is directed into a separation column 170 to remove water and acetic acid as residuum stream 174. The overhead 178 comprises methyl iodide, methyl acetate, and the PRC's. A portion of the overhead 178 may be refluxed back into the separation column as stream 181.

Overhead stream 178 is then directed into the second distillation column 172 as stream 179. Stream 179 is referred to herein as the alternative second column feed stream 179. The feed stream 179 is distilled in the second distillation column 172 to produce the second overhead stream 152 comprising methyl iodide and at least one PRC. Distillation of the alternative second column feed stream 179 further produces residuum stream 154 flowing from the bottom sump zone of column 172 comprising water and greater than or equal to about 0.11 weight percent HI.

Both of these ARS systems are described herein using similar descriptions with like indicators used to describe streams which are essentially identical in each system. The second column overhead 152 and the second column residuum 154 produced using assembly 132 are essentially identical to the same streams 152 and 154 produced using assembly 133. Accordingly, for purposes herein, various flow rates, directing of various streams, and the like are referred to interchangeably between the assemblies shown in 132 and 133. In embodiments, second overhead stream 152 may further comprise dimethyl ether. In embodiments, the process may be operated such that DME is formed in-situ, within the second distillation column 150 or 172. In embodiments in which DME is intentionally formed within the process, DME is known to accumulate in the second column overhead 152, the overhead accumulation tank 160, and the rest of the ARS system.

In embodiments, the second column overhead 152 is condensed and forwarded to an overhead separator 160. A portion of the condensed second column overhead 162 may be refluxed back into the second distillation column (150 or 172) via lines 167 and 164. At least a portion of the condensed second column overhead 162 is cooled (e.g., via heat exchanger 173), and contacted with an aqueous stream 166 (typically water) in at least one extractor 169, typically at an extraction temperature below about 25° C., or below about 20° C., or below 15° C., or below about 10° C., or below about 5° C. However, in embodiments, the extraction temperature may be from 50° C. to 30° C. Extraction of the second column overhead 152 produces an aqueous stream 168 comprising PRC and a small amount of methyl iodide which is subsequently removed from the process as waste. The extraction also produces the raffinate stream 158, which comprises methyl iodide. When the second column overhead 152 comprises dimethyl ether, the raffinate stream 158 also comprises dimethyl ether.

In order to provide adequate and efficient removal of acetaldehyde and other PRC's, the extraction step necessarily requires phase separation between the aqueous phase and the methyl iodide raffinate. Critical to this separation is the density of the two liquids in addition to the partitioning coefficient of the two phases. Water is typically utilized in the extraction, having a density of approximately 1 g/ml. The density of the second column overhead, which is typically 50 wt % or more methyl iodide, may be reduced by the presence of acetaldehyde, methanol, methyl acetate, and other components. Accordingly, the presence of other components in the second column overhead may lead to less efficient separation, or in a worst case, a lack of phase separation. Accordingly, in embodiments, the density of the various streams produced in the aldehyde removal system may be controlled to effect a more efficient removal of acetaldehyde and other PRC's during the extraction process.

In embodiments, the density of the second feed stream 142 to the ARS purification system 108 is from 1.506 to 2.260. In embodiments, the density of the second feed stream 142 is greater than 1.5, or 1.55, or 1.6, or 1.65, or 1.7, or 1.75, or 1.8, or 1.85, or 1.9, or 1.95, or 2.0, and less than 2.3, when determined at process temperatures. In embodiments, the average process temperature of the feed stream 142 feed to the second distillation column is from 50 to 75° C., with 65 to 70° C. being typical.

In embodiments, the density of the second column overhead stream 152 is from 1.1 to 1.7. In embodiments, the density of the second column overhead stream 152 is greater than 1.2, or 1.25, or 1.3, or 1.35, or 1.4, or 1.45, or 1.6, or 1.65, and less than 1.75, when determined at process temperatures. In embodiments, the average process temperature of the second column overhead stream 152 in the overhead receiver 160 is from 35 to 55° C. with 40 to 45° C. being typical.

In embodiments, the density of the second column residuum stream 154 is from 1.3 to 2.1. In embodiments, the density of the second column residuum stream 154 is greater than 1.35, or 1.4, or 1.45, or 1.5, or 1.55, or 1.6, or 1.65, or 1.7, or 1.75, or 1.8, or 1.85, or 1.9, or 1.95, or 2.0, and less than 2.1, when determined at process temperatures. In embodiments, the average process temperature of the second column residuum stream 154 is from 75 to 90° C. with 80 to 85° C. being typical.

In embodiments, the density of the second column overhead stream feed to the extractor 162 after being cooled in heat exchanger 173 is from 1.15 to 1.75. In embodiments, the density of the second column overhead stream feed to the extractor is greater than 1.2, or 1.25, or 1.3, or 1.35, or 1.4, or 1.45, or 1.6, or 1.65, and less than 1.75, when determined at process temperatures. In embodiments, the average temperature of the second column overhead stream feed to the extractor is from 5 to 15° C. with 7 to 12° C. being typical.

In embodiments, the density of the raffinate stream 158 is from 1.7 to 2.3 at process temperatures. In embodiments, the density of raffinate stream 158 is greater than 1.75, or 1.8, or 1.85, or 1.9, or 1.95, or 2.0, or 2.05, or 2.1, or 2.15, or 2.2, or 2.25, and less than 2.3, when determined at process temperatures. In embodiments, the average process temperature of the raffinate is from 10 to 25° C. with 17 to 20° C. being typical. The water stream is typically fed into the extractor at the approximately the same temperature as the second column overhead stream being fed to the extractor. The aqueous stream exits the extractor at a temperature from 20 to 40° C. Likewise, the increased temperature of the raffinate e.g., from 10° C. to 18° C. is due to an exotherm resultant from partitioning of the stream with water during the extraction process.

In embodiments, the density of the second column overhead stream is less than the density of second column feed stream. In embodiments, the percent decrease between the density of the second column feed stream 142 and the density of the second column overhead 152 is from 20% to 35%. In embodiments, this percent decrease is greater than 22%, or 25%, or 30%.

In embodiments, the density of the second column residuum stream is less than the density of second column feed stream. In embodiments, the percent decrease between the density of the second column feed stream 142 and the density of the second column residuum 154 is from 5% to 10%. In embodiments, this percent decrease is greater than 7%, or 9%.

In embodiments, the density of the second column overhead stream feed to the extractor 162 is greater than water. In embodiments, the specific gravity of the second column overhead stream feed to the extractor 162 relative to water is from 1.15 to 1.6, when determined at 10° C. In embodiments, the specific gravity of the second column overhead stream feed to the extractor 162 relative to water is greater than 1.2, or 1.25, or 1.3, or 1.35, or 1.4, or 1.45, or 1.5, or 1.55 and less than 1.6, when determined at the extraction temperature of 10° C.

In embodiments, the density of the raffinate is greater than the density of second column feed stream. In embodiments, the percent increase between the density of the second column feed stream 142 and the density of the raffinate 158 is from 10% to 20%. In embodiments, this percent increase is greater than 12%, or 15%, or 18%, but less than 20%.

In an embodiment, at least a portion of the raffinate stream 158 is recycled back into the second distillation column via line 161, which greatly improves the amount of PRC's present in the second column overhead 152 as is known to one of skill in the art.

In embodiments, the raffinate stream 158 is divided into two portions: a first portion 161 and a second portion 163. The first portion of the raffinate stream flow 161 is recycled back into the second distillation column. The second portion of the raffinate stream flow 163 is recycled back into the reaction medium via stream 155, e.g., via combining stream 155 with stream 116, 118, and/or the like. The recycle of a portion of the raffinate stream back into the reaction medium consumes the DME present in the stream. This prevents excessive accumulation of the DME in the second distillation column 150 or 172, thereby preventing overpressure of the second distillation column 150 or 172 (cf. U.S. Pat. No. 7,223,883). Pressure buildup in column 150 or 172 causes venting of the overhead separator 160 to the scrubber system 139. This venting results in the undesirable recycle of acetaldehyde back into the reaction medium.

In embodiments, a mass flow of the first portion of the raffinate 161 is greater than or equal to a mass flow of the second portion of the raffinate 163. In embodiments, the mass flow of the first portion of the raffinate 161 is greater than or equal to about 1%, or 5%, or 10%, or 20%, or 30%, or 40%, or 50%, or 60%, or 70%, or 80%, or 90%, and less than 500% of the mass flow of the second portion of the raffinate 163. In embodiments, the mass flow of the second portion of the raffinate 163 is greater than or equal to about 1%, or 5%, or 10%, or 20%, or 30%, or 40%, or 50%, or 60%, or 70%, or 80%, or 90%, and less than 500% of the mass flow of the first portion of the raffinate 161.

In embodiments, second distillation column (150 or 172) may optionally comprise a sidestream 157 from which a stream comprising methyl acetate is produced. The optional sidestream 157 allows the second distillation column to be operated under conditions desirable for obtaining a higher concentration of acetaldehyde in the second column overhead stream 152 while providing a mechanism for removing methyl acetate and/or methanol that might otherwise accumulate in the center of the second distillation column (e.g., a methyl acetate bulge) which is eventually pushed into the second column overhead stream 152. The optional sidestream 157, comprising methyl acetate, if utilized, is preferably recycled back into the process.

Embodiments of the instant process may further comprise directing a top flush stream 164 comprising water into the distillation zone of the second distillation column 150 or 172. The top flush stream 164 may comprise fresh material, but is preferably generated from a stream produced by the process to control water content in the system. In embodiments, the top flush stream 164 comprises water, acetic acid, methanol, or any combination thereof.

In embodiments utilizing assembly 133, a portion of the separation column residuum stream 174 may be directed via stream 156 and 164 into the alternative second distillation column 172 as the top flush stream 164. In embodiments in which apparatus 132 is utilized, the top flush stream may include at least a portion of residuum stream 154, directed via stream 156 to 164. In embodiments, top flush stream 164 may include a portion of the light phase overhead stream 135, e.g., via a portion of stream 114 consisting mainly of the light phase 135 being directed into 164.

In embodiments, the mass flow rate of the top flush stream 164 is greater than or equal to about 1% of the total mass flow rate of feed stream 142, the second column feed stream 143, or feed stream 179 where applicable. In embodiments, the mass flow rate of the top flush stream 164 is greater than or equal to about 5%, or 10%, or 20%, or 30%, or 40%, or 50%, or 60%, or 70%, or 80%, or 90%, 100%, or 150%, and less than 500% of the mass flow of feed stream 142, the second column feed stream 143, or feed stream 179 where applicable.

In an embodiment, the process may further comprise directing a bottom flush stream 165 into the distillation zone of the second distillation column and/or into the bottom sump zone of the second distillation column. The bottom flush stream 165 may comprise, water, acetic acid, or both. In embodiments, bottom flush stream 165 comprises at least 10 wt %, or 20 wt %, or 30 wt %, or 40 wt %, or 50 wt %, or 60 wt %, or 70 wt %, or 80 wt %, or 90 wt %, or 95 wt % acetic acid. In embodiments, the bottom flush stream consists of, or consists essentially of acetic acid.

In embodiments, the mass flow rate of the bottom flush stream 165 into the second distillation column 150 or 172 is greater than or equal to about 0.1% of the total mass flow rate of feed stream 142, or the second column feed stream 143 or 179. In embodiments, the mass flow rate of the bottom flush stream 165 is greater than or equal to about 5%, or 10%, or 20%, or 30%, or 40%, or 50%, or 60%, or 70%, or 80%, or 90%, 100%, or 150%, or 200%, or 300%, and less than 500% of the mass flow of feed stream 142, the second column feed stream 143, or feed stream 179 where applicable.

In embodiments wherein the second column feed stream is, or is derived from the heavy phase 137, the water content in the second distillation column may be insufficient to result in HI in ionized form dissociated in the aqueous phase. Accordingly, the bottom sump zone of the distillation column may have a water concentration below about 5 wt %, or 4 wt %, or less such that the HI is present as hydrogen iodide vapor and thus, the HI will distill overhead with the second column overhead stream instead of being concentrated in the bottom sump zone. In such embodiments, the amount of aqueous top flush may be adjusted to ensure the HI present and produced within the second distillation column is present as an ionized or dissociated aqueous solution. In addition, or instead, the bottom flush may comprise water sufficient to produce a bottom residuum stream comprising HI. The bottom flush stream may be added just above the inlet of the feed stream to the second distillation column such that HI produced therein is present in the bottom sump zone of the distillation column. Likewise, the bottom flush stream may be added directly to the bottom sump zone to maintain the HI concentration as selected levels in the bottom residuum stream.

In embodiments, the total combined mass flow rates of the top flush stream 164 and the bottom flush stream 165 is about 1.1%, or 5%, or 10%, or 20%, or 30%, or 40%, or 50%, or 60%, or 70%, or 80%, or 90%, 100%, or 150%, or 200%, or 300%, and less than 500% of the mass flow of feed stream 142, the second column feed stream 143, or feed stream 179 where applicable.

In embodiments, the mass flow rate of the top flush stream 164, the mass flow rate of the bottom flush stream 165, or the total combined mass flow rates of the top flush stream 164 and the bottom flush stream 165 is from about 1% to about 50% of the mass flow rate of the residuum stream 154.

In embodiments, second distillation column residuum stream 154 comprises water, acetic acid, and at least about 0.11 weight percent HI. In embodiments, residuum stream 154 comprises greater than or equal to about 5 wt % water, or 10 wt %, or 20 wt %, or 30 wt %, or 40 wt %, or 50 wt %, or 60 wt %, or 70 wt %, or 80 wt %, or 90 wt %, or 95 wt % water. In embodiments, residuum stream 154 comprises greater than or equal to about 5 weight percent acetic acid, or 10 wt %, or 20 wt %, or 30 wt %, or 40 wt %, or 50 wt %, or 60 wt %, or 70 wt %, or 80 wt %, or 90 wt %, or 95 wt % acetic acid. In embodiments, residuum stream 154 comprises greater than or equal to about 5 wt % methyl iodide, or 10 wt %, or 20 wt %, or 30 wt %, or 40 wt %, or 50 wt %, or 60 wt %, or 70 wt %, or 80 wt %, or 90 wt %, or 95 wt % methyl iodide.

In embodiments, the second column residuum stream 154 comprises greater than or equal to about 0.11 weight percent HI. In an embodiment, the residuum stream 154 comprises greater than or equal to about 0.21 weight percent HI, or greater than or equal to about 0.25 weight percent HI, or greater than or equal to about 0.3 weight percent HI, or greater than or equal to about 0.35 weight percent HI, or greater than or equal to about 0.4 weight percent HI, or greater than or equal to about 0.5 weight percent HI, or greater than or equal to about 0.6 weight percent HI, or greater than or equal to about 0.65 weight percent HI, or greater than or equal to about 0.7 weight percent HI.

In embodiments, HI is produced within the second distillation column, typically through the hydrolysis of methyl iodide into methanol and HI. Accordingly, more HI exits the distillation column (150 or 172) via overhead stream 152 and/or residuum stream 154 than enters the column in the column feed stream 142. Corrosion considerations render excessive amounts of HI generally undesirable. As discussed above, a certain amount of HI, controlled within a specific range, is desirable in order to catalyze the formation of a controlled amount of DME within the column. This DME has been found to have a beneficial effect on phase separation in the liquid-liquid extraction system common to acetaldehyde removal systems as exemplified in U.S. Pat. No. 7,223,883, U.S. Pat. No. 7,223,886, and U.S. Pat. No. 8,076,507. In embodiments, the residuum stream 154 comprises less than or equal to about 10 weight percent HI, or less than or equal to about 5 weight percent HI, or less than or equal to about 2 weight percent HI, or less than or equal to about 1.5 weight percent HI, or less than or equal to about 1.2 weight percent HI, or less than or equal to about 1.1 weight percent HI, or less than or equal to about 1.0 weight percent HI, or less than or equal to about 0.9 weight percent HI, or 0.75 weight percent HI, or less than or equal to about 0.7 weight percent HI, or less than or equal to about 0.65 weight percent HI, or less than or equal to about 0.6 weight percent HI, or less than or equal to about 0.55 weight percent HI, or less than or equal to about 0.5 weight percent HI, or less than or equal to about 0.45 weight percent HI, based on the total weight of the residuum stream. The maximum concentration of HI in the second column residuum stream 154 may be selected according to an acceptable level of corrosion under the conditions present therein. Accordingly, selection of particular materials may allow for even higher concentrations of HI in the residuum above 0.11 wt %.

In embodiments, residuum stream 154 may further comprise methyl iodide, methanol, methyl acetate, and/or acetaldehyde. In embodiments, a portion of residuum stream 154 may be directed to drying column 130, e.g. via reflux derived from drying column decanter 148, to the reactor 104, or both.

Figure 3:
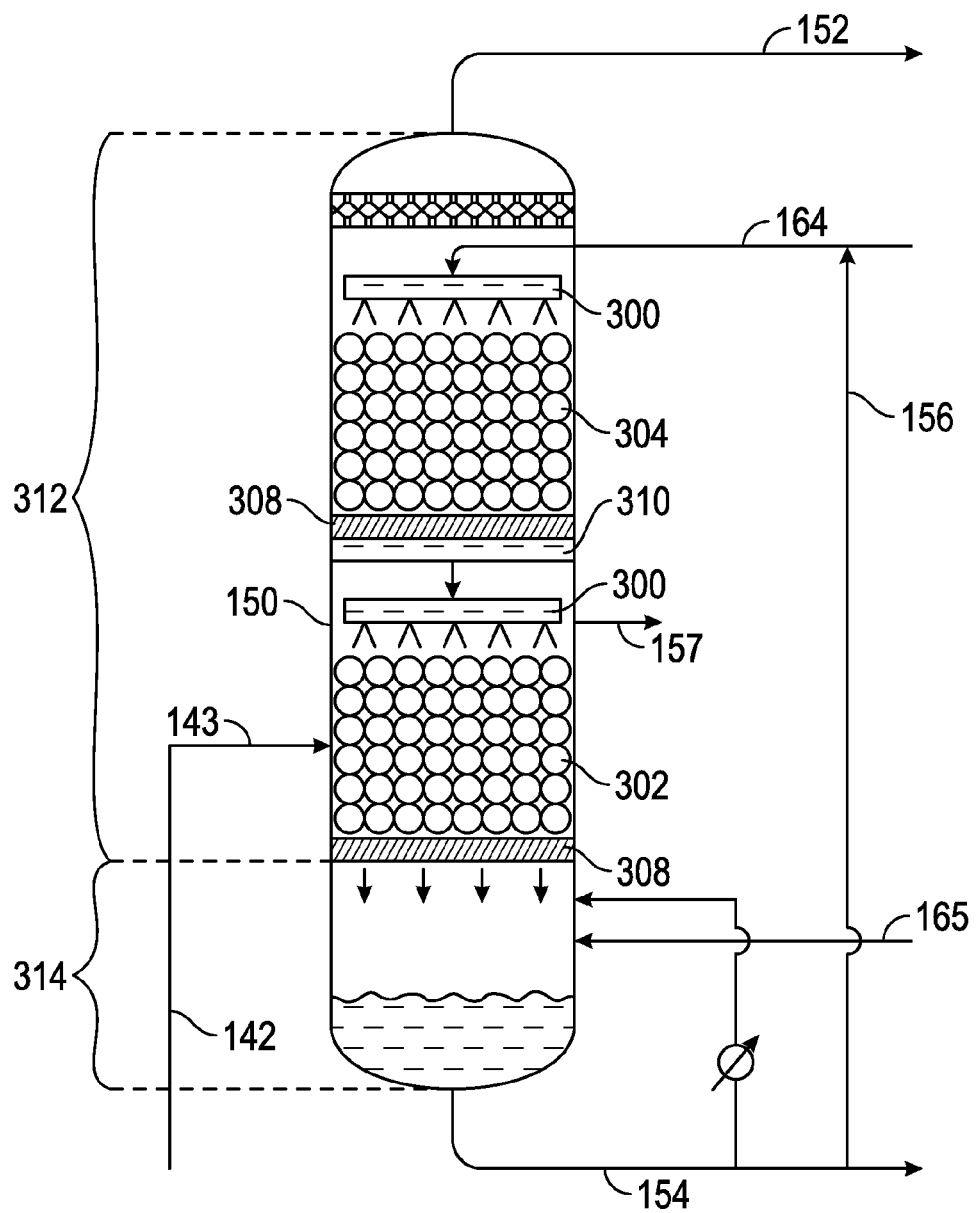
FIG. 3 is a cross sectional diagram of a second distillation column according to an embodiment.

As shown in FIG. 3, in an embodiment, the second distillation column (FIG. 3 shows column 150 which for purposes of the figures is representative of either 150 or 172) comprises a distillation zone 312 and a bottom sump zone 314. The distillation zone 312 is everything above the bottom sump zone 314, and may comprise various internal components including, but not limited to packing sections, liquid collectors/redistributors, trays, supports, and the like.

In embodiments, the second distillation column contains at least 100 trays and is operated at a temperature ranging from about 101° C. at the bottom to about 60° C. at the top. In an alternative embodiment, the second distillation column comprises structured packing in place of trays. In embodiments, the structured packing, a random packing, or a combination thereof, having an interfacial area of 150 to 400 $m^2/m^3$, and may comprise ceramic, polymeric, an austenitic-ferritic metallic alloy, or a combination thereof. In embodiments, a bottom temperature of the second distillation column is from about 90° C. to about 130° C., a pressure of the second distillation column is from atmospheric pressure or about 150 kPa above atmospheric pressure, to about 700 kPa above atmospheric pressure, or a combination thereof.

In embodiments, the distillation zone is dimensioned and arranged to control the contact time between methyl iodide and water to control the concentration of HI in the second distillation column residuum 154.

In embodiments, the liquid phase present within the second distillation column comprises a first liquid phase comprising greater than about 50 weight percent water (an aqueous or water phase) and a second liquid phase comprising greater than about 50 weight percent methyl iodide (a methyl iodide phase).

In embodiments, the distillation zone 312, and in particular various internal components within the distillation zone, are dimensioned and arranged to control the contact time between the methyl iodide phase and the water phase to the minimum amount required to produce a second column residuum stream 154 having an HI concentration greater than or equal to about 0.11 weight percent.

In embodiments, the internal components are designed (dimensioned and arranged) to minimize the residence time of the liquid phases present within the distillation column under process conditions. It has been discovered that a minimum contact time between the aqueous phase and the methyl iodide phase within the second distillation column is necessary to produce a residuum stream flowing from the bottom sump zone comprising water and greater than or equal to about 0.11 weight percent HI. However, it has also been discovered that prolonged contact time between discrete portions of the aqueous phase and the methyl iodide phase adversely affect the ability to control the amount of HI in the residuum stream. Such prolonged contact time may result from pooling and/or trapping of discrete portions of a particular phase within particular internal components of the column, without affecting the overall residence time of the liquid phase within the distillation column.

As shown in FIG. 3, in embodiments, the second distillation column 150 or 172 may comprises a plurality of internal components which may include liquid collectors 310, liquid distributors 300, and the like, which may be dispersed between a plurality of packing sections 302 and 304 each individually comprising structured packing, random packing, or a combination thereof. In alternative embodiments, the internal components may be distillation plates or trays, along with various supports 308 and collectors.

In embodiments, the distillation zone 312 comprises a vapor phase and a liquid phase, the liquid phase comprising a first liquid phase 326 (cf. FIG. 4) and a second liquid phase 328 (cf. FIG. 4), wherein the first liquid phase comprises greater than about 50 weight percent water and the second liquid phase comprises greater than about 50 weight percent methyl iodide. Apart from some intra-solubility, the two liquid phases are generally immiscible.

Figure 4:
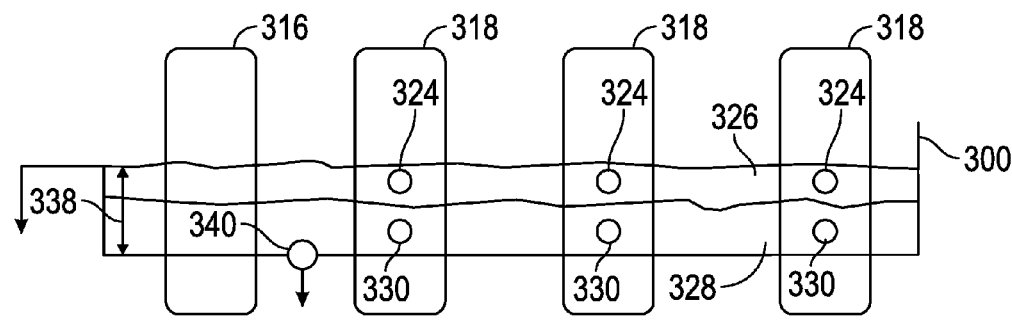
FIG. 4 is a cross sectional diagram of a liquid redistributor of a second distillation column according to an embodiment.

As shown in FIG. 4, each internal component includes an associated or corresponding liquid phase retention volume which is dependent on the dimensions and arrangement of the component. In embodiments in which two liquid phases are present within the distillation column, the total retention volume of the liquid phase associated with a particular component is equal to the sum of the retention volume of the first liquid phase 326 and the retention volume of the second liquid phase 328 within the confines of the particular component. The liquid holdup volume of the distillation zone is thus equal to the sum of each of the liquid phase retention volumes of the components within the distillation zone plus the amount present on the sides and other non-functional surfaces of the column.

Each component retention volume has a corresponding residence time of the first liquid phase and a corresponding residence time of the second liquid phase under operational conditions. The residence time of a particular liquid phase in an internal component is equal to the average time a discrete amount of that particular liquid phase is retained within the component's retention volume under operational conditions. However, the physical properties of the two liquid phases, the position of drains or flow paths of the internal component, and/or other aspects of the internal component may result in pooling or trapping of one of the liquid phases within its retention volume. A liquid phase which becomes trapped within the retention volume of a particular component may have an average residence time within that particular component which exceeds the average residence time of the entire liquid phase in the distillation zone of the column.

Accordingly, the residence times of particular liquid phases within the internal components of a distillation column must be measured directly or calculated/and or modeled under operational conditions based on the physical properties of the liquid phases and the design and arrangement of the particular components.

As shown in FIG. 4 since two liquid phases 326 and 328 are present during the distillation, column internals which do not include bottom drains, or which do not comprise adequately sized or positioned bottom drains will tend to accumulate the heavier methyl iodide second liquid phase 328 beneath the lighter aqueous first liquid phase 326, even though the methyl iodide phase has a lower boiling point than the aqueous phase. The heavier methyl iodide phase will then tend to progress through the column when carried along with the lighter aqueous phase. The heavier phase may also accumulate in a retention volume and then overflow the various structures within the column. Such column designs result in prolonged and unpredictable residence times for discrete portions of the second liquid phase.

Likewise, as show in FIG. 4, column internals which include bottom drains but which do not include top drains, or which do not comprise adequately sized or positioned top drains will tend to accumulate the lighter aqueous first liquid phase 326 within the retention volume of the internal component. The first liquid phase 326 may then become trapped relative to the better drained heavier second liquid phase 328, which drains through the accumulated first liquid phase 326 and through one or more bottom drain holes 340. The lighter first liquid phase will then tend to progress through the column only when carried along with the heavy phase, or by overflowing the various structures within the column, leading to prolonged residence times for discrete portions of the first aqueous liquid phase within the retention volume of certain internal component structures.

As shown in FIG. 4, in an embodiment, a liquid redistributor, tray, or other column internal 300 may include one or more vapor risers 316 which allow the vapor phase to flow through the structure, and one or more drip tubes 318 to allow liquid to pass through the structure from one side to another. In an embodiment, one or more drip tubes 318 may each comprise at least one of a first plurality of passages 324, disposed there-through which are holes arranged to drain the first liquid phase 326, which is less dense (lighter) than the second liquid phase 328, and thus located farther away from bottom of the structure. Each drip tube 318 may further comprises at least one of a second plurality of passages 330 disposed there-through, which are holes arranged proximate to the bottom of the structure to drain the second heavier liquid phase 328 there-through.

Figure 5:
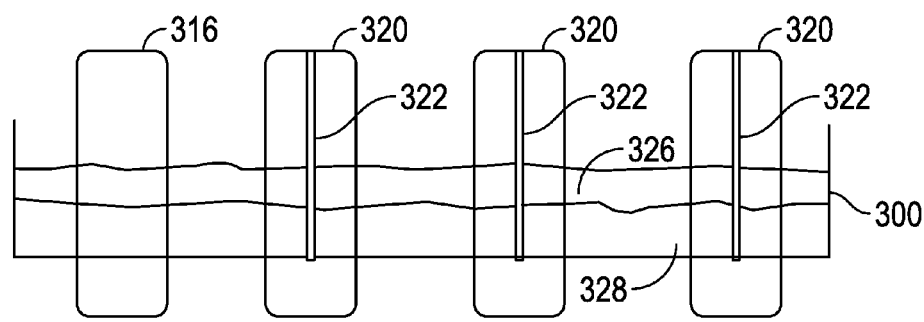
FIG. 5 is a cross sectional diagram of a liquid redistributor of a second distillation column according to another embodiment.

FIG. 5 shows an embodiment wherein each of the drip tubes 320 comprise at least one of the first plurality of passages which are combined with the second plurality of passages in the form of a slit 332 disposed there through along a vertical wall of the drip tube 320 which allows both the first light phase 326 and the second heavy phase 328 to drain through the structure.

Figure 6:
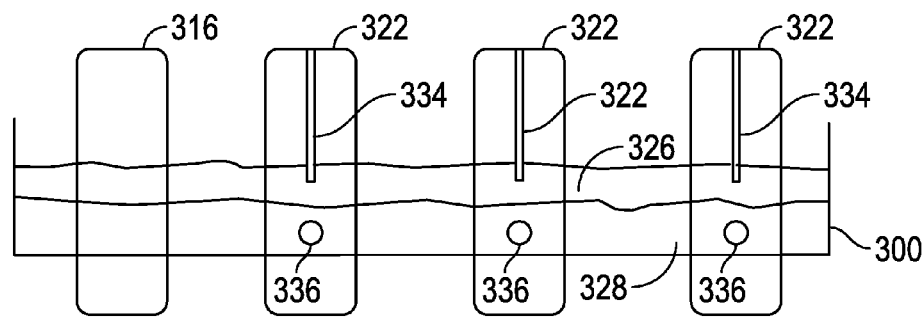
FIG. 6 is a cross sectional diagram of a liquid redistributor of a second distillation column according to another embodiment.

FIG. 6 shows an embodiment wherein each of the drip tubes 322 comprise at least one of the first plurality of passages in the form of a slit 334 disposed there through along only a portion of a vertical wall of the drip tube 322, which is arranged to allow the first light phase 326 to drain through the structure, and each drip tube 322 may further comprises at least one of a second plurality of passages 336 disposed there-through, which are holes arranged proximate to the bottom of the structure to drain the second heavier liquid phase 328 there through.

In embodiments, as shown in FIG. 4, a structure may comprise a weir or dam having a side height 338 (e.g., a side of a liquid redistributor 300 or a column tray) which allows the lighter first phase 326 to drain by spilling over the side, in combination with the tray being equipped with one or more bottom drain holes 340 to allow the heavy phase to drain there-through.

In embodiments, the column packing, when present, may also be selected to reduce liquid holdup, as is generally understood by one having reasonable skill in the art, and the like.

Experiments were conducted by simulation to determine the average residence time of the aqueous phase of a second distillation column operated using a top flush stream and partial column reflux in an aldehyde removal system of a commercial acetic acid production process, which produced a residuum stream having an HI concentration which was difficult to control. In comparative examples, an average residence time of the aqueous phase in the distillation zone of the second distillation column which only included bottom drains in the liquid redistributors was determined by simulation to be about 6 hours, which was not reflected in the total residence time of the feed stream in the distillation column. Accordingly, the aqueous phase was being trapped in portions of the column. The column was then simulated to be equipped with drip tubes configured with a first and a second plurality of fluid passages as shown in FIGS. 4, 5, and 6 in separate modeling experiments. Under the same conditions as the comparative example simulation, the average residence time of the aqueous phase in the distillation zone of the inventive distillation columns was reduced from about 6 hours to about 11 minutes on average.

Employment of a second distillation column according to embodiments disclosed herein having an average liquid phase residence time within the distillation zone of about 1 minute to about 60 minutes, wherein the distillation zone comprised a plurality of internal components, each having a component liquid retention volume, wherein each of the internal components was dimensioned and arranged such that an average residence time of the first liquid phase and an average residence time of the second liquid phase in each of the component liquid retention volumes was less than about 30 minutes, resulted in a second column residuum stream having a concentration of HI between 0.11 weight percent and 0.9 weight percent.

In embodiments, the average residence time of the feed stream within the distillation zone of the second distillation column is about 1 minute to about 60 minutes or about 1 minute to about 30 minutes, or about 1 minute to about 15 minutes.

In embodiments the distillation zone comprises a plurality of internal components, each having a component liquid retention volume. Each of the internal components is dimensioned and arranged such that an average residence time of the first liquid phase within the liquid retention volume of each component is less than about 30 minutes, or about 20 minutes, or about 10 minutes, or about 5 minutes. In embodiments, each of the internal components is dimensioned and arranged such that an average residence time of the second liquid phase within the liquid retention volume of each component is less than about 30 minutes, or about 20 minutes, or about 10 minutes, or about 5 minutes, when determined via modeling or direct measurement.

In embodiments, at least one internal component, or all internal components present in the distillation zone is (are) dimensioned and arranged such that the average residence time of the first liquid phase is greater than or equal to the average residence time of the second liquid phase in the corresponding component liquid retention volume when determined via modeling or direct measurement.

In embodiments, at least one internal component e.g., a distillation tray, liquid collector, distributor, or redistributor, comprises a first plurality of flow paths (e.g., 324, 322, and/or 334) dimensioned and arranged such that the average residence time of the first liquid phase is from about 0.1 minutes to about 20 minutes, or to about 10 minutes, or to about 5 minutes in the corresponding component liquid retention volume when determined via modeling or direct measurement.

In embodiments, the at least one internal component further comprises a second plurality of flow paths (e.g., 330, 322, 336 and/or 340) dimensioned and arranged such that the average residence time of the second liquid phase is from about 0.1 minutes to about 20 minutes, or to about 10 minutes, or to about 5 minutes in the corresponding component liquid retention volume when determined via modeling or direct measurement.

In embodiments, the concentration of HI in the second column residuum may be controlled by selecting various conditions associated with the second distillation column. In embodiments, the concentration of HI in the second column residuum may be controlled between 0.1 wt % and 0.9 wt % by selecting the temperature and pressures of the distillation, i.e., the bottom temperature of the second distillation column and the pressure of the second distillation column.

In embodiments, the concentration of HI in the second column residuum may be controlled by selecting the composition of the top flush stream, the mass flow rate of the top flush stream, the composition of the bottom flush stream, and/or the mass flow rate of the bottom flush stream. For example, to decrease the concentration of HI in the second column residuum, the amount of bottom flush stream relative to the column feed rate may be increased to dilute and wash out the HI present in the column sump.

In embodiments, the concentration of HI in the second column residuum may be controlled by selecting an average liquid phase residence time in the distillation zone, and/or by controlling the average residence time of one or more liquid phases within the retention volumes of one or more internal components, as discussed herein. In addition, any combination of the above control schemes may be selected to produce the residuum stream comprising about 0.11 weight percent HI to less than or equal to 0.9 weight percent HI.

In embodiments, the process for producing acetic acid may further include introducing a lithium compound into the reactor to maintain the concentration of lithium acetate in an amount from 0.3 to 0.7 wt % in the reaction medium. In embodiments, an amount of the lithium compound is introduced into the reactor to maintain the concentration of hydrogen iodide in an amount from 0.1 to 1.3 wt % in the reaction medium. In embodiments, the concentration of the rhodium catalyst is maintained in an amount from 300 to 3000 wppm in the reaction medium, the concentration of water is maintained in amount from 0.1 to 4.1 wt % in the reaction medium, and the concentration of methyl acetate is maintained from 0.6 to 4.1 wt % in the reaction medium, based on the total weight of the reaction medium present within the carbonylation reactor.

In embodiments, the lithium compound introduced into the reactor is selected from the group consisting of lithium acetate, lithium carboxylates, lithium carbonates, lithium hydroxide, other organic lithium salts, and mixtures thereof. In embodiments, the lithium compound is soluble in the reaction medium. In an embodiment, lithium acetate dihydrate may be used as the source of the lithium compound.

Lithium acetate reacts with hydrogen iodide according to the following equilibrium reaction (I) to form lithium iodide and acetic acid:

$$\text{LiOAc} + \text{HI} \rightleftharpoons \text{LiI} + \text{HOAc} \qquad (I)$$

Lithium acetate is thought to provide improved control of hydrogen iodide concentration relative to other acetates, such as methyl acetate, present in the reaction medium. Without being bound by theory, lithium acetate is a conjugate base of acetic acid and thus reactive toward hydrogen iodide via an acid-base reaction. This property is thought to result in an equilibrium of the reaction (I) which favors reaction products over and above that produced by the corresponding equilibrium of methyl acetate and hydrogen iodide. This improved equilibrium is favored by water concentrations of less than 4.1 wt % in the reaction medium. In addition, the relatively low volatility of lithium acetate compared to methyl acetate allows the lithium acetate to remain in the reaction medium except for volatility losses and small amounts of entrainment into the vapor crude product. In contrast, the relatively high volatility of methyl acetate allows the material to distill into the purification train, rendering methyl acetate more difficult to control. Lithium acetate is much easier to maintain and control in the process at consistent low concentrations of hydrogen iodide. Accordingly, a relatively small amount of lithium acetate may be employed relative to the amount of methyl acetate needed to control hydrogen iodide concentrations in the reaction medium. It has further been discovered that lithium acetate is at least three times more effective than methyl acetate in promoting methyl iodide oxidative addition to the rhodium [I] complex.

In embodiments, the concentration of lithium acetate in the reaction medium is maintained at greater than or equal to 0.3 wt. %, or greater than or equal to 0.35 wt. %, or greater than or equal to 0.4 wt. %, or greater than or equal to 0.45 wt. %, or greater than or equal to 0.5 wt. %, and/or in embodiments, the concentration of lithium acetate in the reaction medium is maintained at less than or equal to 0.7 wt. %, or less than or equal to 0.65 wt. %, or less than or equal to 0.6 wt. %, or less than or equal to 0.55 wt. %, when determined according to perchloric acid titration to a potentiometric endpoint.

It has been discovered that an excess of lithium acetate in the reaction medium can adversely affect the other compounds in the reaction medium, leading to decrease productivity. Conversely, it has been discovered that a lithium acetate concentration in the reaction medium below about 0.3 wt. % results in a lack of control over hydrogen iodide concentrations within the reaction medium.

In embodiments, the lithium compound may be introduced continuously or intermittently into the reaction medium. In embodiments, the lithium compound is introduced during reactor start up. In embodiments, the lithium compound is introduced intermittently to replace entrainment losses.

A series of experiments conducted to demonstrate the promotional effect of lithium acetate in the carbonylation reactor and to determine the effect of lithium acetate on the methyl iodide oxidative addition to the rhodium complex, $Li[RhI_2(CO)_2]$ confirmed the promotional effect of lithium acetate on reaction rates. A linear increase of reaction rates correlated to increasing lithium acetate concentrations was observed. This correlation was indicative of first order promotional effects of reaction between methyl iodide and $Li[RhI_2(CO)_2]$. These experiments further showed a non-zero intercept, confirming that lithium acetate is not required for the MeI—Rh(I) reaction to occur, but the lithium acetate does give considerable promotional effect even at low concentrations.

In embodiments, the process may further comprise maintaining a butyl acetate concentration in the acetic acid product at 10 wppm or less without directly removing butyl acetate from the product acetic acid. In embodiments, the butyl acetate concentration in the final acetic acid product may be maintained below 10 ppm by removing acetaldehyde from the reaction medium, e.g., removing acetaldehyde from a stream derived from the reaction medium, and/or by controlling the reaction temperature, and/or the hydrogen partial pressure, and/or the metal catalyst concentration in the reaction medium. In embodiments, the butyl acetate concentration in the final acetic acid product is maintained by controlling one or more of the carbonylation reaction temperature from 150° C. to 250° C., the hydrogen partial pressure in the carbonylation reactor at from 0.3 to 2 atm, the rhodium metal catalyst concentration in the reaction medium at from 100 to 3000 wppm, based on the total weight of the reaction medium, and/or the acetaldehyde concentration in the reaction medium at 1500 ppm or less.

In embodiments, the acetic acid product formed according to embodiments of the process disclosed herein has a butyl acetate concentration of less than or equal to 10 wppm, or less than or equal to 9 wppm, or less than or equal to 8 wppm, or less than or equal to 6 wppm, or less than or equal to 2 wppm, based on the total weight of the acetic acid product. In embodiments, the acetic acid product is substantially free of butyl acetate, i.e., a butyl acetate concentration of less than 0.05 wppm or is non-detectable by detection means known in the art. In embodiments, the acetic acid product may also have a propionic acid concentration of less than 250 wppm, or less than 225 ppm, or less than 200 wppm.

In embodiments, the butyl acetate concentration in the acetic acid product may be controlled by controlling the concentration of acetaldehyde in the reaction medium. While not wishing to be bound by theory, butyl acetate is thought to be a by-product caused by aldol condensation of acetaldehyde. Applicant has discovered that by maintaining the acetaldehyde concentration in the reaction medium at less than 1500 wppm, the concentration of butyl acetate in the final acetic acid product may be controlled below 10 wppm. In embodiments, the acetaldehyde concentration in the reaction medium is maintained at less than or equal to 1500 wppm, or less than or equal to 900 wppm, or less than or equal to 500 wppm, or less than or equal to 400 wppm, based on the total weight of the reaction medium.

In embodiments, the butyl acetate concentration in the acetic acid product may be controlled by controlling the reaction temperature of the carbonylation reactor at a temperature greater than or equal to 150° C., or 180° C., and less than or equal to 250° C., or 225° C.; and/or the hydrogen partial pressure in the carbonylation reactor may be controlled at greater than or equal to 0.3 atm, or 0.35 atm, or 0.4 atm, or 0.5 atm, and less than or equal to 2 atm, or 1.5 atm, or 1 atm.

While relatively high hydrogen partial pressure results in improved reaction rates, selectivity, improved catalyst activity, and reduced temperatures, applicant has discovered that as hydrogen partial pressure is increased, impurity production is also increased, including butyl acetate.

In embodiments, the hydrogen partial pressure may be controlled by modifying the amount of hydrogen present in the carbon monoxide source and/or by increasing or decreasing the reactor vent flows to obtain the desired hydrogen partial pressure within the carbonylation reactor.

A series of experiments were conducted to demonstrate the effect of hydrogen partial pressure and acetaldehyde concentration in the reaction medium on the concentration of butyl acetate in the final acetic acid product. These experiments confirmed a correlation between reduced butyl acetated concentrations in the final acetic acid product, and relatively low acetaldehyde concentrations in the reaction medium and/or relatively low hydrogen partial pressures in the carbonylation reactor. Experiments in which the acetaldehyde concentration in the reactor was maintained below 1500 ppm and the reactor hydrogen partial pressure maintained below 0.6 atm resulted in butyl acetate levels below 10 wppm in the final acetic acid product. Other experiments showed an acetaldehyde concentration in the reactor below 1500 wppm and a reactor hydrogen partial pressure of 0.46 atm resulted in a butyl acetate concentration of less than 8 wppm in the final acetic acid product. Similar conditions in which the hydrogen partial pressure was 0.30 atm resulted in butyl acetate levels below 6 wppm, and hydrogen partial pressures of 0.60 atm resulted in butyl acetate concentrations below 0.2 wppm in the final acetic acid product. However, comparative experiments in which the hydrogen partial pressure was 0.4 and 0.3 respectively, but in the absence of an aldehyde removal system such that the acetaldehyde concentrations in the reactor exceeded 1500 wppm, resulted in a final acetic acid product having butyl acetate levels of 13 wppm and 16 wppm respectively.

Applicant has further discovered that the concentration of propionic acid in the final acetic acid product may be affected by the concentration butyl acetate in the acetic acid product. Accordingly, by controlling the butyl acetate concentration in the final acetic acid product to 10 wppm or less, the concentration of propionic acid in the final acetic acid product may be controlled to less than 250 wppm, or less than 225 ppm, or less than 200 wppm. Likewise, by controlling the ethanol content in the reactor feed, which may be present as an impurity in the methanol source, the propionic acid and butyl acetate concentrations in the final acetic acid product may also be controlled. In embodiments, the concentration of ethanol in the methanol feed to the carbonylation reactor is controlled to less than or equal to 150 wppm. In embodiments, if present, the ethanol concentration in the methanol feed to the reactor is less than or equal to 100 wppm, or 50 wppm, or 25 wppm.

Applicant has further discovered that the formation of ethyl iodide may be affected by numerous variables, including the concentration of acetaldehyde, ethyl acetate, methyl acetate and methyl iodide in the reaction medium. Additionally, ethanol content in the methanol source, hydrogen partial pressure and hydrogen content in the carbon monoxide source have been discovered to affect ethyl iodide concentration in the reaction medium and, consequently, propionic acid concentration in the final acetic acid product.

In embodiments, the concentration of ethyl iodide in the reaction medium is maintained/controlled to be less than or equal to 750 wppm, or less than or equal to 650 wppm, or less than or equal to 550 wppm, or less than or equal to 450 wppm, or less than or equal to 350 wppm. In alternative embodiments, the concentration of ethyl iodide in the reaction medium is maintained/controlled at greater than or equal to 1 wppm, or 5 wppm, or 10 wppm, or 20 wppm, or 25 wppm, and less than or equal to 650 wppm, or 550 wppm, or 450 wppm, or 350 wppm.

In embodiments, the propionic acid concentration in the acetic acid product may further be maintained below 250 wppm by maintaining the ethyl iodide concentration in the reaction medium at less than or equal to 750 wppm without removing propionic acid from the acetic acid product.

In embodiments, the ethyl iodide concentration in the reaction medium and propionic acid in the acetic acid product may be present in a weight ratio from 3:1 to 1:2, or from 5:2 to 1:2, or from 2:1 to 1:2. In embodiments, the acetaldehyde:ethyl iodide concentration in the reaction medium is maintained at a weight ratio from 2:1 to 20:1, or from 15:1 to 2:1, or from 9:1 to 2:1.

In embodiments, the ethyl iodide concentration in the reaction medium may be maintained by controlling at least one of the hydrogen partial pressure, the methyl acetate concentration, the methyl iodide concentration, and/or the acetaldehyde concentration in the reaction medium.

A series of experiments conducted to determine the effect of acetaldehyde and other reaction conditions on the formation of ethyl indicated a relationship between acetaldehyde concentration and ethyl iodide concentration in the reaction medium, as well as relationships between the reactor concentration of ethyl iodide and the concentration of propionic acid in the final acetic acid product. In general, an ethyl iodide concentration of less than 750 wppm and an acetaldehyde concentration of less than 1500 wppm in the reaction medium resulted in propionic acid concentrations of less than 250 wppm in the acetic acid product.

As is evident from the figures and text presented above, a variety of embodiments are contemplated.

E1. A process comprising:
  a. providing a feed stream having a first density comprising water, acetic acid, methyl acetate, at least one PRC, and greater than about 30 wt % methyl iodide to a distillation column comprising a distillation zone and a bottom sump zone; and
  b. distilling the feed stream at a pressure and a temperature sufficient to produce an overhead stream having a second density and comprising greater than about 40 wt % methyl iodide and at least one PRC; wherein a percent decrease between the first density and the second density is from 20% to 35%.

E2. The process according to embodiment E1, wherein the specific gravity of the second density relative to water is from 1.15 to 1.6, when determined at 10° C.

E3. The process according to embodiment E1 or E2, wherein a residuum stream flowing from the bottom sump zone has a third density which is less than the first density, and comprises greater than about 0.1 wt % water.

E4. The process according to any one of embodiments E1 to E3, wherein the residuum stream comprises greater than or equal to about 0.11 wt % HI.

E4.1 The process according to embodiment E4, wherein at least a portion of the HI is produced within the distillation column.

E5. The process according to any one of embodiments E1 to E4.1, wherein a percent decrease between the first density and the third density is from 5% to 10%.

E6. The process according to any one of embodiments E1 to E5, wherein distillation of the feed stream produces a first liquid phase comprising greater than about 50 weight percent water and a second liquid phase comprising greater than about 50 weight percent methyl iodide within the distillation zone, and wherein the distillation zone comprises a plurality of internal components, each having a component liquid retention volume, and wherein an average residence time of the first liquid phase and an average residence time of the second liquid phase in each of the component liquid retention volumes is less than about 30 minutes.

E7. The process according to embodiment E6, wherein the average residence time of the second liquid phase is greater than or equal to the average residence time of the first liquid phase in at least one component liquid retention volume.

E8. The process according to any one of embodiments E1 to E7, further comprising directing a top flush stream comprising water into the distillation zone at a mass flow rate which is greater than or equal to about 0.1 percent of the mass flow rate of the feed stream.

E9. The process according to embodiment E8, wherein the top flush stream comprises a portion of the bottom residuum stream.

E10. The process according to any one of embodiments E1 to E9, further comprising directing a bottom flush stream comprising acetic acid, water, or both into the bottom sump zone at a mass flow rate which is greater than or equal to about 0.1 percent of the mass flow rate of the feed stream.

E11. The process according to any one of embodiments E1 to E11, wherein the overhead stream comprises dimethyl ether.

E11.1 The process according to any one of embodiments E1 to E11, wherein the overhead stream comprises from 0.1 wt % to 50 wt % dimethyl ether.

E11.2 The process according to embodiments E11 or E11.1, wherein at least a portion of the dimethyl ether is produced within the distillation column.

E12. A process comprising:
  a. carbonylating a reaction medium comprising a reactant feed stream comprising methanol, methyl acetate, dimethyl ether, or mixtures thereof, water, a rhodium catalyst, an iodide salt and methyl iodide in a reactor to form acetic acid;
  b. distilling a stream derived from the reaction medium in a first column to yield an acetic acid side stream which is further purified to produce a product acetic acid stream, and a first overhead stream comprising methyl iodide, water, acetic acid, methyl acetate, and at least one PRC;
  c. biphasically separating the first overhead stream into a light phase comprising methyl iodide, acetic acid, methyl acetate, at least one PRC, and greater than about 30 wt % water, and a heavy phase comprising water, acetic acid, methyl acetate, at least one PRC, and greater than about 30 wt % methyl iodide;

d. directing a second column feed stream comprising or derived from the heavy phase into a second distillation column comprising a distillation zone and a bottom sump zone;

e. distilling the second column feed stream at a pressure and a temperature sufficient to produce a second overhead stream having a second density and which comprises greater than about 40 wt % methyl iodide and at least one PRC, and a residuum stream flowing from the bottom sump zone having a third density which is less than the first density, and which comprises greater than about 0.1 wt % water, wherein a percent decrease between the first density and the second density is from 20% to 35%;

f. extracting at least a portion of the second column overhead stream comprising methyl iodide and at least one PRC with water to produce an aqueous stream comprising the at least one PRC, and a raffinate stream having a fourth density which is greater than the first density, and which comprises greater than about 90 wt % methyl iodide; and g. directing at least a first portion of the raffinate stream back into the distillation zone of the second distillation column.

E13. The process according to embodiments E12, wherein the specific gravity of the second density relative to water is from 1.15 to 1.6 when determined at 10° C.

E14. The process according to embodiments E12 or E13, wherein a percent increase between the first density and the fourth density is from 10% to 20%.

E15. The process according to any one of embodiments E12 to E14, further comprising directing a top flush stream comprising water into the distillation zone of the second distillation column at a mass flow rate of greater than or equal to about 0.1 percent of the mass flow rate of the second column feed stream, wherein the top flush stream comprises a portion of the bottom residuum stream, at least a portion of the first portion of the raffinate stream, a portion of the light phase separated from the first overhead stream, or a combination thereof.

E16. The process according to any one of embodiments E12 to E15, further comprising directing a bottom flush stream comprising acetic acid, water, or both into the bottom sump zone of the second distillation column at a mass flow rate of greater than or equal to about 0.1 percent of the mass flow rate of the second column feed stream.

E17. The process according to any one of embodiments E12 to E16, wherein the second column overhead stream comprises dimethyl ether and further comprising directing a second portion of the raffinate stream comprising methyl iodide and dimethyl ether back into the reaction medium.

E18. The process according to embodiment E17, wherein a mass flow rate of the first portion of the raffinate stream is greater than or equal to a mass flow rate of the second portion of the raffinate stream.

E19. The process according to any one of embodiments E12 to E18, wherein a bottom temperature of the second distillation column is about 70° C. to about 100° C.

E20. The process according to any one of embodiments E12 to E19, wherein a top temperature of the second distillation column is about 40° C. to about 60° C.; wherein a pressure of the second distillation column is from atmospheric pressure to about 700 kPa above atmospheric pressure.

E21. The process according to any one of embodiments E12 to E20, wherein an HI concentration in the reaction medium is from 0.1 to 1.3 wt %.

E22. The process according to any one of embodiments E12 to E21, wherein the rhodium catalyst concentration in the reaction medium is from 300 to 3000 wppm.

E23. The process according to any one of embodiments E12 to E22, wherein the water concentration in the reaction medium is from 0.1 to 4.1 wt %.

E24. The process according to any one of embodiments E12 to E23, wherein the methyl acetate concentration in the reaction medium is from 0.6 to 4.1 wt %.

E25. The process according to any one of embodiments E12 to E14, wherein a hydrogen partial pressure in the reactor is from 0.3 to 2 atm.

E26. The process according to any one of embodiments E12 to E25, further comprising introducing a lithium compound selected from the group consisting of lithium acetate, lithium carboxylates, lithium carbonates, lithium hydroxide, and mixtures thereof into the reactor to maintain the concentration of lithium acetate from 0.3 to 0.7 wt % in the reaction medium.

E27. The process according to any one of embodiments E12 to E26, further comprising controlling a butyl acetate concentration in the acetic acid product stream at 10 wppm or less without directly removing butyl acetate from the acetic acid product.

E28. The process according to embodiment E27, wherein the butyl acetate concentration in the acetic acid product stream is controlled by maintaining an acetaldehyde concentration in the reaction medium at 1500 ppm or less.

E29. The process according to embodiment E27 or E28, wherein the butyl acetate concentration in the acetic acid product stream is controlled by controlling a temperature in the carbonylation reactor from 150 to 250° C.

E30. The process according to any one of embodiments E27 to E29, wherein the butyl acetate concentration in the acetic acid product stream is controlled by controlling a hydrogen partial pressure in the reactor from 0.3 to 2 atm.

E31. The process according to any one of embodiments E27 to E30, wherein the butyl acetate concentration in the acetic acid product stream is controlled by controlling a rhodium metal catalyst concentration in the reaction medium from 100 to 3000 wppm, based on the total weight of the reaction medium.

E32. The process according to any one of embodiments E12 to E31, further comprising controlling an ethyl iodide concentration in the reaction medium at less than or equal to 750 wppm.

E33. The process according to any one of embodiments E12 to E32, further comprising controlling the propionic acid to less than 250 wppm without directly removing propionic acid from the acetic acid product.

E34. The process according to embodiment E32 or E33, wherein ethyl iodide in the reaction medium and propionic acid in the acetic acid product are present in a weight ratio from 3:1 to 1:2.

E35. The process according to any one of embodiments E32 to E34, wherein acetaldehyde and ethyl iodide are present in the reaction medium in a weight ratio from 2:1 to 20:1.

E36. The process according to any one of embodiments E32 to E35, wherein the methanol source of the carbonylation reactor comprises less than 150 wppm ethanol.

E37. The process according to any one of embodiments E32 to E36, wherein the ethyl iodide concentration in the reaction medium is controlled by controlling a hydrogen partial pressure in the carbonylation reactor.

E38. The process according to any one of embodiments E32 to E37, wherein the ethyl iodide concentration in the reaction medium is controlled by controlling a methyl acetate concentration in the reaction medium.

E39. The process according to any one of embodiments E32 to E38, wherein the ethyl iodide concentration in the reaction medium is controlled by controlling a methyl iodide concentration in the reaction medium.

E40. The process according to any one of embodiments E12 to E39, wherein the second overhead stream comprises from 0.1 wt % to 50 wt % dimethyl ether.

E41. The process according to embodiment E40, wherein at least a portion of the dimethyl ether is produced within the distillation column.

E42. The process according to any one of embodiments E12 to E41, wherein the residuum stream flowing from the sump of the second distillation column comprises greater than or equal to about 0.11 wt % HI.

E43. The process according to embodiment E42, wherein at least a portion of the HI is produced within the distillation column.

While the embodiments have been illustrated and described in detail in the drawings and foregoing description, the same is to be considered as illustrative and not restrictive in character, it being understood that only some embodiments have been shown and described and that all changes and modifications that come within the spirit of the embodiments are desired to be protected. It should be understood that while the use of words such as ideally, desirably, preferable, preferably, preferred, more preferred or exemplary utilized in the description above indicate that the feature so described may be more desirable or characteristic, nonetheless may not be necessary and embodiments lacking the same may be contemplated as within the scope of the invention, the scope being defined by the claims that follow. In reading the claims, it is intended that when words such as "a," "an," "at least one," or "at least one portion" are used there is no intention to limit the claim to only one item unless specifically stated to the contrary in the claim.

We claim:

1. A process comprising:
   a. providing a feed stream having a first density comprising water, acetic acid, methyl acetate, at least one PRC, and greater than about 30 wt % methyl iodide to a second distillation column comprising a distillation zone and a bottom sump zone; and
   b. distilling the feed stream at a pressure and a temperature sufficient to produce a second column overhead stream having a second density and comprising greater than about 40 wt % methyl iodide and at least one PRC;
   wherein a percent decrease between the first density and the second density is from 20% to 35%;
   wherein the feed stream is derived from an overhead of a first distillation column in which a reaction product is distilled to produce acetic acid as a sidestream, wherein a residuum stream flowing from the bottom sump zone has a third density which is less than the first density, and comprises greater than about 0.1 wt % water, and greater than or equal to about 0.11 wt % HI.

2. The process of claim 1, wherein the specific gravity of the second density relative to water is from 1.15 to 1.6, when determined at 10° C.

3. The process of claim 1, wherein a percent decrease between the first density and the third density is from 5% to 10%.

4. The process of claim 1, wherein distillation of the feed stream produces a first liquid phase comprising greater than about 50 weight percent water and a second liquid phase comprising greater than about 50 weight percent methyl iodide within the distillation zone, and wherein the distillation zone comprises a plurality of internal components, each having a component liquid retention volume, and wherein an average residence time of the first liquid phase and an average residence time of the second liquid phase in each of the component liquid retention volumes is less than about 30 minutes.

5. The process of claim 4, wherein the average residence time of the second liquid phase is greater than or equal to the average residence time of the first liquid phase in at least one component liquid retention volume.

6. The process of claim 1, further comprising directing a top flush stream comprising water into the distillation zone at a mass flow rate which is greater than or equal to about 0.1 percent of the mass flow rate of the feed stream.

7. The process of claim 6, wherein the top flush stream comprises a portion of the bottom residuum stream.

8. The process of claim 1, further comprising directing a bottom flush stream comprising acetic acid, water, or both into the bottom sump zone at a mass flow rate which is greater than or equal to about 0.1 percent of the mass flow rate of the feed stream.

9. The process of claim 1, wherein the overhead stream comprises dimethyl ether.

10. A process comprising:
    a. carbonylating a reaction medium comprising a reactant feed stream comprising methanol, methyl acetate, dimethyl ether, or mixtures thereof, water, a rhodium catalyst, an iodide salt and methyl iodide in a reactor to form acetic acid;
    b. distilling a stream derived from the reaction medium in a first column to yield an acetic acid side stream which is further purified to produce a product acetic acid stream, and a first overhead stream comprising methyl iodide, water, acetic acid, methyl acetate, and at least one PRC;
    c. biphasically separating the first overhead stream into a light phase comprising methyl iodide, acetic acid, methyl acetate, at least one PRC, and greater than about 30 wt % water, and a heavy phase comprising water, acetic acid, methyl acetate, at least one PRC, and greater than about 30 wt % methyl iodide;
    d. directing a second column feed stream comprising or derived from the heavy phase into a second distillation column comprising a distillation zone and a bottom sump zone;
    e. distilling the second column feed stream at a pressure and a temperature sufficient to produce a second overhead stream having a second density and which comprises greater than about 40 wt % methyl iodide and at least one PRC, and a residuum stream flowing from the bottom sump zone having a third density which is less than the first density, and which comprises greater than about 0.1 wt % water and greater than or equal to about 0.11 wt % HI, wherein a percent decrease between the first density and the second density is from 20% to 35%;

f. extracting at least a portion of the second column overhead stream comprising methyl iodide and at least one PRC with water to produce an aqueous stream comprising the at least one PRC, and a raffinate stream having a fourth density which is greater than the first density, and which comprises greater than about 90 wt % methyl iodide; and g. directing at least a first portion of the raffinate stream back into the distillation zone of the second distillation column.

11. The process of claim 10, wherein the specific gravity of the second density relative to water is from 1.15 to 1.6 when determined at 10° C.

12. The process of claim 10, wherein a percent increase between the first density and the fourth density is from 10% to 20%.

13. The process of claim 10, further comprising directing a top flush stream comprising water into the distillation zone of the second distillation column at a mass flow rate of greater than or equal to about 0.1 percent of the mass flow rate of the second column feed stream, wherein the top flush stream comprises a portion of the bottom residuum stream, at least a portion of the first portion of the raffinate stream, a portion of the light phase separated from the first overhead stream, or a combination thereof.

14. The process of claim 10, further comprising directing a bottom flush stream comprising acetic acid, water, or both into the bottom sump zone of the second distillation column at a mass flow rate of greater than or equal to about 0.1 percent of the mass flow rate of the second column feed stream.

15. The process of claim 10, wherein the second column overhead stream comprises dimethyl ether and further comprising directing a second portion of the raffinate stream comprising methyl iodide and dimethyl ether back into the reaction medium.

16. The process of claim 15, wherein a mass flow rate of the first portion of the raffinate stream is greater than or equal to a mass flow rate of the second portion of the raffinate stream.

17. The process of claim 10, wherein:

a bottom temperature of the second distillation column is about 70° C. to about 100° C., a top temperature of the second distillation column is about 40° C. to about 60° C., a pressure of the second distillation column is from atmospheric pressure to about 700 kPa above atmospheric pressure, an HI concentration in the reaction medium is from 0.1 to 1.3 wt %, the rhodium catalyst concentration in the reaction medium is from 300 to 3000 wppm, the water concentration in the reaction medium is from 0.1 to 4.1 wt %, the methyl acetate concentration in the reaction medium is from 0.6 to 4.1 wt %, a hydrogen partial pressure in the reactor is from 0.3 to 2 atm, or any combination thereof.

18. The process of claim 10, further comprising:

i. introducing a lithium compound selected from the group consisting of lithium acetate, lithium carboxylates, lithium carbonates, lithium hydroxide, and mixtures thereof into the reaction medium to maintain a concentration of lithium acetate between 0.3 and 0.7 wt % in the reaction medium, ii. controlling a butyl acetate concentration in the product acetic acid stream at 10 wppm or less without directly removing butyl acetate from the product acetic acid stream, iii. controlling an ethyl iodide concentration in the reaction medium at less than or equal to 750 wppm, or any combination thereof.

* * * * *